US007446097B2

(12) United States Patent
Mercep et al.

(10) Patent No.: US 7,446,097 B2
(45) Date of Patent: *Nov. 4, 2008

(54) CONJUGATES OF IMMUNE CELL SPECIFIC MACROLIDE COMPOUNDS WITH ANTI-INFLAMMATORY COMPOUNDS FOR IMPROVED CELLULAR TARGETING OF ANTI-INFLAMMATORY THERAPY

(75) Inventors: Mladen Mercep, Zagreb (HR); Milan Mesic, Zagreb (HR); Linda Tomaskovic, Zagreb (HR); Marijana Komac, Zagreb (HR); Boska Hrvacic, Velika Gorica (HR); Stribor Markovic, Karlovac (HR)

(73) Assignee: Glaxosmithkline Istrazivacki Centar Zagreb D.O.O, Zagreb (HR)

( * ) Notice: Subject to any disclaimer, the term of this patent is extended or adjusted under 35 U.S.C. 154(b) by 742 days.

This patent is subject to a terminal disclaimer.

(21) Appl. No.: 10/250,934

(22) PCT Filed: Jan. 3, 2002

(86) PCT No.: PCT/HR02/00001

§ 371 (c)(1),
(2), (4) Date: Dec. 29, 2003

(87) PCT Pub. No.: WO02/055531

PCT Pub. Date: Jul. 18, 2002

(65) Prior Publication Data

US 2004/0198677 A1    Oct. 7, 2004

(30) Foreign Application Priority Data

Jan. 9, 2001    (HR) .......................... P 20010018 A

(51) Int. Cl.
A61K 31/70    (2006.01)
C07H 17/08    (2006.01)
(52) U.S. Cl. ......................................... 514/29; 536/7.4
(58) Field of Classification Search .................. 536/7.4; 514/29
See application file for complete search history.

(56) References Cited

U.S. PATENT DOCUMENTS 4,710,495 A    12/1987  Bodor
6,566,509 B1 *  5/2003  Griffin et al. .................. 536/7.4

FOREIGN PATENT DOCUMENTS

| EP | 0283055 B1 | 8/1990 |
|----|-----------|--------|
| EP | 0771564 A1 | 5/1997 |
| EP | 0774589 A1 | 5/1997 |
| FR | 2776927 A | 10/1999 |
| JP | 1-163124 | 6/1989 |
| WO | 9213872 A1 | 8/1992 |
| WO | 9213873 A1 | 8/1992 |
| WO | 9413690 A1 | 6/1994 |
| WO | 9414834 A1 | 7/1994 |
| WO | WO-97/41255 | 11/1997 |
| WO | 9964040 A1 | 12/1999 |
| WO | 0042055 A1 | 7/2000 |
| WO | 03/070174 | 8/2003 |

OTHER PUBLICATIONS

Anderson, R. et al., "An in-vitro evaluation of the cellular uptake and intraphagocytic bioactivity of clarithromycin (A-56268, TE-031), a new macrolide antimicrobial agent," Journal of Antimicrobial Chemotherapy, 1988 22, pp. 923-933.

Fietta, A. et al., "Requirements for Intracellular Accumulation and Release of Clarithromycin and Azithromycin by Human Phagocytes," Journal of Chemotherapy, 1997, vol. 9—n.1, pp. 23-31.

Schentag, J.J. et al., "Relationships Between Serum, Intracellular, and Infection Site Concentrations of Macrolide and Azalide Antibiotics: A Theoretical Exploration of the Concept of White Blood Cell Drug Delivery to Infection Sites," Antiinfective Drugs and Chemotherapy, 1996, vol. 14, No. 2, pp. 137-146.

Vazifeh, D. et al., "Cellular Accumulation of the New Ketolide RU 64004 by Human Neutrophils: Comparison with That of Azithromycin and Roxithromycin," Antimicrobial Agents and Chemotherapy, Oct. 1997, vol. 41, No. 10, pp. 2099-2107.

Romo, D. et al., "Total Synthesis and Immunosuppressive Activity of (−)-Pateamine A and Related Compounds: Implementation of a β-Lactam-Based Macrocyclization," Journal of American Chemical Society, 1998, 120, pp. 12237-12254.

Griffith, E. et al., "[7] Yeast Three-Hybrid System for Detecting Ligand-Receptor Interactions," Methods in Enzymology, 2000, vol. 328, pp. 89-103.

Abdelghaffar et al.; "Erythromycin A-Derived Macrolides Modify the Functional Activites of Human Neutrophils by Altering the Phospholipase D-Phosphatidate Phosphohydrolase Transduction Pathway: L-Cladinose Is Involved Both in ALterations of Neutrophil Functions and Modulation of This Transductional Pathway"; Journal of Immunology; 1997; vol. 159, No. 8; pp. 3995-4005.

Agouridas et al.; "Synthesis and Antibacterial Activity of Ketolides (6-O-Methyl-3-Oxoerythromycin Derivatives): A New Class Antibacterials Highly Potent Against Macrolide-Resistant and Susceptible Respiratory Pathogens"; Journal of Medicinal Chemistry; 1998; vol. 41, No. 21; pp. 4080-4100.

Geerdes-Fenge H F et al.; "Comparative Pharmacokinetics of Dirithromycin and Erythromycin in Normal Volunteers with Special Regard to Accumulation in Polymorphonuclear Leukocytes and in Saliva"; European Journal of Clinical Pharmacology; 1997; vol. 53, No. 2; pp. 127-133.

Glaude et al.; "In Vitro and In Vivo Uptake of Azithromycin (CP-62,993) by Phagocytic Cells: Possible Mechanism of Delivery and Release at Sites of Infection"; Antimicrobial Agents and Chemotherapy; 1989; Vol. 33, No. 3; pp. 277-282.

(Continued)

Primary Examiner—Elli Peselev
(74) Attorney, Agent, or Firm—J. Michael Strickland

(57) ABSTRACT

The present invention relates to novel compounds represented by the structure I and pharmaceutical preparations thereof for the treatment of inflammatory diseases in humans and animals.

43 Claims, No Drawings

OTHER PUBLICATIONS

Ianaro et al.; "Anti-Inflammatory Activity of Macrolide Antibiotics"; Journal of Pharmacology and Experimental Therapeutics; 2000; vol. 292, No. 1; pp. 156-163.

Kertesz et al.; "Thiol Esters from Steroid 17β-Carboxylic Acids: Carboxylate Activation and Internal Participation by 17α-Acylates"; Journal of Organic Chemistry; 1986; vol. 51; pp. 2315-2328.

Khosla et al.; "Streptogramins: a New Class of Antibiotics"; Indian Journal of Medical Sciences; 1999; vol. 53, No. 3; pp. 111-119.

Labro; "Anti-Inflammatory Activity of Macrolides: A New Therapeutic Potential?"; Journal of Antmicrobial Chemotherapy; 1998; vol. 41, Suppl. B; pp. 37-46.

Little et al.; "Soft Drugs Based on Hydrodortisone: the Inactive Metabolite Approach and Its Application to Steroidal Antiinflammatory Agents"; Pharmaceutical Research; 1999; vol. 16, No. 6; pp. 961-967.

McLean et al.; "Novel Fluorinated Antiinflammatory Steroid with Reduced Side Effects: Methyl 9α-Fluoroprednisolone-16-Carboxylate"; Journal of Pharmaceutical Sciences; 1994; vol. 83, No. 4; pp. 476-480.

Mikasa et al.; "The Anti-Inflammatory Effect of Erythromycin in Zymosan-Induced Peritonitis of Mice"; Journal of Antmicrobial Chemotherapy; 1992; vol. 30; pp. 339-348.

Olsen et al.; "Intrapulmonary Pharmacokinetics of Azithromycin in Healthy Volunteers Given Five Oral Doses"; Antimicrobial Agents and Chemotherapy; 1996; vol. 40, No. 11; pp. 2582-2585.

Scorneaux et al.; "Intracellular Accumlation, Subcellular Distribution, and Efflux of Tilmicosin in Bovine Mammary, Blood, and Lung Cells."; Journal of Diary Science; 1999; vol. 82, No. 6; pp. 1202-1212.

Suzuki et al.; "General and Facile Method for Determination of Configuration of Steriod-17-yl Methyl Glycolates at C-20 Based on Kinetic Examination"; Journal of the Chemical Society, Perkin Transactions I; 1998; pp. 3831-3836.

Takizawa et al.; "Erythromycin Modulates IL-8 Expression in Normal and Inflamed Human Bronchial Epithelial Cells"; American Journal of Respiratory and Critical Care Medicine; 1997; vol. 156, No. 1; pp. 266-271.

Travers; "Novel Immunomodulators for Topical Skin Diease Therapy"; Expert Opinion on Investigational Drugs; 2000; vol. 9, No. 3; pp. 529-542

U.S. Appl. No. 10/830,858 filed Apr. 22, 2004.
U.S. Appl. No. 11/201,685 filed Aug. 10, 2005.
U.S. Appl. No. 11/355,808 filed Feb. 15, 2006.
U.S. Appl. No. 11/718,505 filed May 2, 2007.
U.S. Appl. No. 11/813,882 filed Jul. 13, 2007.
U.S. Appl. No. 11/813,884 filed Jul. 13, 2007.

* cited by examiner

CONJUGATES OF IMMUNE CELL SPECIFIC MACROLIDE COMPOUNDS WITH ANTI-INFLAMMATORY COMPOUNDS FOR IMPROVED CELLULAR TARGETING OF ANTI-INFLAMMATORY THERAPY

CROSS REFERENCE TO RELATED APPLICATIONS

This application is 371 Application of PCT/HR02/00001, filed 3 Jan. 2002 which claims priority to Croatian Patent Application number P2001018A, filed 9 Jan. 2002.

TECHNICAL PROBLEM

The present invention relates to new anti-inflammatory compounds represented by the general structure I, to their salts and solvates, to processes for their preparation and to the use of these compounds in the treatment of inflammatory diseases and conditions in humans and animals.

PRIOR ART

Anti-inflammatory medicaments could be classified into those of steroid and of nonsteroid type. Steroid anti-inflammatory compounds are still the most effective ones in the treatment of inflammatory diseases and conditions such as asthma, chronic obstructive pulmonary disease, inflammatory nasal diseases such as allergic rhinitis, nasal polyps, intestinal diseases such as Crohn's disease, colitis, ulcerative colitis, dermatological inflammations such as eczema, psoriasis, allergic dermatitis, neurodermatitis, pruritis, conjunctivitis and rheumatoid arthritis. In addition to the excellent potency and effectiveness, medicaments of this type also possess numerous unfavourable effects e.g. on carbohydrate metabolism, calcium resorption, secretion of endogenous corticosteroids as well as on physiological functions of hypophysis, adrenal cortex and thymus. Hitherto developed steroids are highly effective against inflammation conditions and processes since they inhibit many inflammation mediators whereas their systemic unfavourable effects are diminished. Patent applications WO 94/13690, WO 94/14834, WO 92/13873 and WO 92/13872 disclose so-called "soft" steroids or hydrolysable corticosteroids designed for topical application on the inflammation site, whereas their systemic unfavourable effect is diminished due to the instability of "soft" steroids in serum, wherein the active steroid very rapidly hydrolizes into the inactive form. An ideal steroid, however, without unfavourable effects in a long-term and continuous treatment as required for the control of diseases such as asthma or Crohn's disease has yet to be found and it has been worked intensively on finding and developing steroids with an improved therapeutic profile.

Nonsteroid anti-inflammatory medicaments of different mechanisms act on particular inflammation mediators, thus providing a therapeutical effect. Due to different action mechanisms and differences in the inhibition of particular inflammation mediators, the steroid and nonsteroid medicaments possess different profiles of anti-inflammation effects, hence in particular conditions they are used alternatively or preferentially. Unfortunately, nonsteroid anti-inflammatory medicaments are not absolutely specific either and demonstrate unfavourable effects when used in greater concentrations or over long periods. It is known that many nonsteroid anti-inflammatory medicaments act as inhibitors of endogenous COX-1 enzyme, which is very important in maintaining the integrity of the gastric mucosa. Thus, the use of these medicaments causes injuries of the gastric mucosa and bleeding in numerous patients. For some anti-inflammatory compounds (theophylline) it is known that their therapeutic index is very narrow, which limits their usage.

Macrolide antibiotics accumulate within different cells of organism, especially within phagocyte cells such as mononuclear peripheral blood cells, peritoneal and alveolar macrophages as well as in the liquid surrounding the bronchoalveolar epithelium (Glaude R. P. et al, *Antimicrob. Agents Chemother.*, 33 1989, 277-282; Olsen K. M. et al, *Antimicrob. Agents Chemother.*, 40 1996, 2582-2585). Moreover, in the literature also relatively weak inflammatory effects of some macrolides are described. Thus, there has recently been described the anti-inflammatory effect of erythromycin derivatives (*J. Antimicrob. Chemother.*, 41, 1998, 37-46; WO 00/42055) and azithromycin derivatives (EP 0283055). An anti-inflammatory effect of some macrolides is also known from in vitro and in vivo studies in experimental animals such as at zimosane-induced peritonitis in mice (*J. Antimicrob. Chemother.* 30, 1992, 339-348) and at endotoxine-induced neutrophil accumulation in rat trachea (*J. Immunol.* 159, 1997, 3395-4005). The modulating effect of macrolides upon cytokines such as interleukin 8 (IL-8) (*Am. J. Respir. Crit. Care. Med.* 156, 1997, 266-271) or interleukin 5 (IL-5) (EP 0775489 and EP 0771564) is known as well.

TECHNICAL SOLUTION

Compounds of the structure I differ from hitherto known ones in their new action mechanism characterized by selective accumulation in the organs and cells targeted in the above-mentioned inflammation conditions and diseases. Such action of the new compounds represented by the structure I arises from the macrolide portion M due to the said specific pharmacokinetic properties. Such pharmacokinetic properties enable the compounds represented by the structure I to act exclusively in the inflammation site just in the inflammation cells themselves by inhibiting the production of inflammation mediators. In such a manner the unfavourable systemic effect of both corticosteroids and nonsteroid anti-inflammatory compounds is avoided. After topical application the molecules rapidly accumulate in inflammation cells, wherein they act by inhibiting the production of cytokines and chemokines as well as other inflammation mediators and thus suppressing the inflammation. According to the known and established prior art, the compounds represented by the structure I, which are the object of the present invention, their pharmacologically acceptable salts and pharmaceutical preparations comprising them have hitherto not been described. Moreover, none of the compounds being the object of the present invention has been described either as an anti-inflammatory substance or as an inhibitor of eosinophilic accumulation in inflammation tissues.

The object of the present invention are new compounds, their salts and solvates represented by the structure I

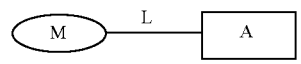

wherein M represents a macrolide subunit possessing the property of accumulation in inflammatory cells, A represents an anti-inflammatory subunit that can be steroid or nonsteroid and L represents a chain linking M and A, as well as an improved therapeutic effect of these compounds in treating inflammation diseases and conditions.

More specifically, this invention relates to compounds, their salts and solvates represented by the structure I, wherein M represents a macrolide subunit represented by the formulas

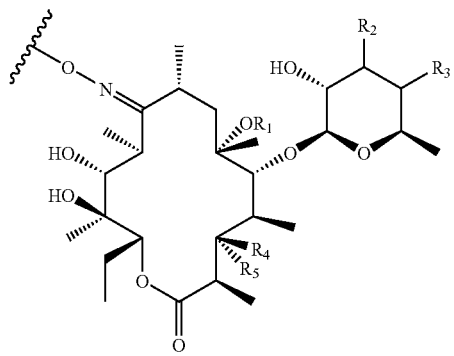

M1 wherein
$R_1$ is hydrogen or a methyl group,
$R_2$ and $R_3$ are both hydrogen or together form a bond, or
  $R_2$ is an amino group represented by the substructure

—NR'R"

wherein R' and R" may be, independently from each other, hydrogen or any alkyl or cycloalkyl group having 1-6 carbon atoms, with the proviso that $R_3$ is then hydrogen,
$R_4$ is a hydroxyl or cladinosyl group represented by the structure

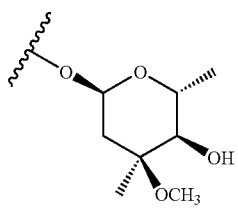

$R_4$ and $R_5$ may also together form a carbonyl group, with the proviso that $R_1$ is then a methyl group;

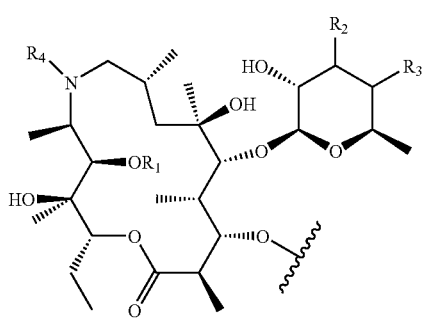

M2 wherein
$R_1$ is hydrogen or a methyl group,
$R_2$ and $R_3$ are both hydrogen or together form a bond, or
  $R_2$ is an amino group represented by the substructure

—NR'R"

wherein R' and R" may be, independently from each other, hydrogen or any allyl or cycloalkyl group having 1-6 carbon atoms, with the proviso that $R_3$ is then hydrogen,
$R_4$ may be any alkyl group having 1-4 carbon atoms, preferably a methyl group;

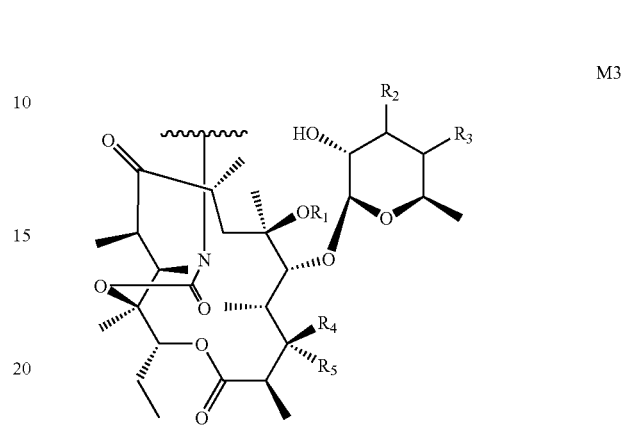

M3 wherein
$R_1$ is hydrogen or a methyl group,
$R_2$ and $R_3$ are both hydrogen or together form a bond, or
  $R_2$ is an amino group represented by the substructure

—NR'R"

wherein R' and R" may be, independently from each other, hydrogen or any alkyl or cycloalkyl group having 1-6 carbon atoms, with the proviso that $R_3$ is then hydrogen,
$R_4$ is a hydroxyl or cladinosyl group represented by the structure

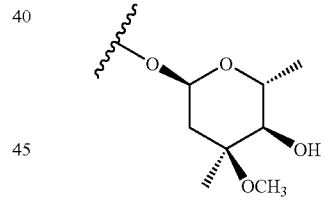

$R_4$ and $R_5$ may also together form a carbonyl group, with the proviso that $R_1$ is then a methyl group;

M4 wherein
$R_1$ is hydrogen or a methyl group,
$R_2$ and $R_3$ are both hydrogen or together form a bond, or
$R_2$ is an amino group represented by the substructure

—NR'R"

wherein R' and R" may be, independently from each other, hydrogen or any alkyl or cycloalkyl group having 1-6 carbon atoms, with the proviso that $R_3$ is then hydrogen, $R_4$ is a hydroxyl or cladinosyl group represented by the structure

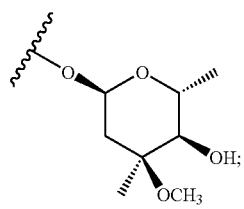

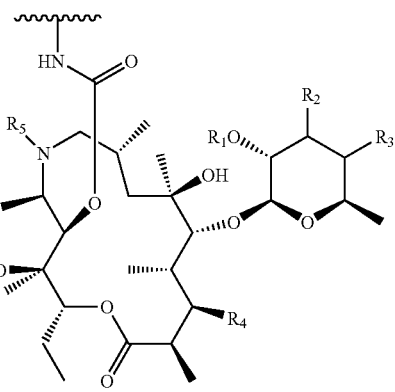
M5 wherein
$R_1$ is hydrogen or a methyl group,
$R_2$ and $R_3$ are both hydrogen or together form a bond, or
$R_2$ is an amino group represented by the substructure

—NR'R"

wherein R' and R" may be, independently from each other, hydrogen or any alkyl or cycloalkyl group having 1-6 carbon atoms, with the proviso that $R_3$ is then hydrogen, $R_4$ is a a hydroxyl or cladinosyl group represented by the structure

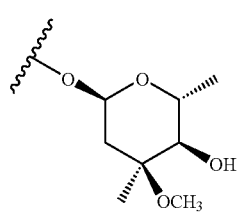

$R_5$ may be any alkyl group having 1-4 carbon atoms, preferably a methyl group;

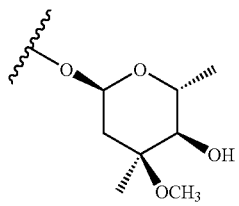
M6 wherein
$R_1$ is hydrogen or an acetyl group,
$R_2$ and $R_3$ are both hydrogen or together form a bond, or
$R_2$ is amino group represented by the substructure

—NR'R"

wherein R' and R" may be, independently from each other, hydrogen or any alkyl or cycloalkyl group having 1-6 carbon atoms, with the proviso that $R_3$ is then hydrogen, $R_4$ is a hydroxyl or cladinosyl group represented by the structure

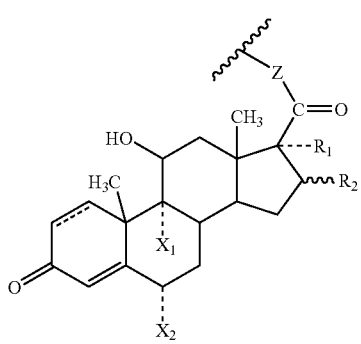

$R_5$ may be any alkyl group having 1-4 carbon atoms, preferably a methyl group,
and A is an anti-inflammatory subunit represented by the formulas:

A1 wherein Z represents oxygen or a NH group, $R_1$ is hydrogen or a hydroxyl or O-acyl or O-alkyl group, $R_2$ represents hydrogen or a methyl group, which may be oriented in α- or β-position, $X_1$ is hydrogen or halogen, $X_2$ is hydrogen or halogen, with halogen meaning fluorine, chlorine or bromine, 1,2-position may represent a double or a single carbon-carbon bond;

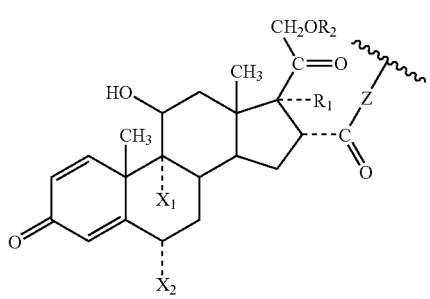

A2 wherein Z represents oxygen or a NH group, $R_1$ is hydrogen or a hydroxyl or O-acyl or O-alkyl group, $R_2$ represents hydrogen or an acyl group, $X_1$ is hydrogen or halogen, $X_2$ is hydrogen or halogen, with halogen meaning fluorine, chlorine or bromine;

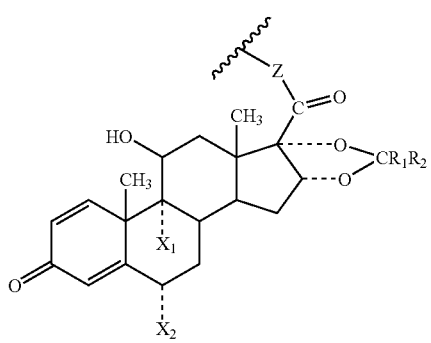

A3 or stereoisomeric forms thereof, wherein the 1,2-position represents a saturated or unsaturated double bond, wherein Z represents oxygen or a NH group, $R_1$ is hydrogen, a straight or branched hydrocarbon chain having 1-4 carbon atoms, $R_2$ is hydrogen, a straight or branched hydrocarbon chain having 1-10 carbon atoms, with the proviso that $R_1$ and $R_2$ are not simultaneously hydrogen, $X_1$ is hydrogen or halogen, $X_2$ is hydrogen or halogen, with halogen meaning fluorine, chlorine or bromine;

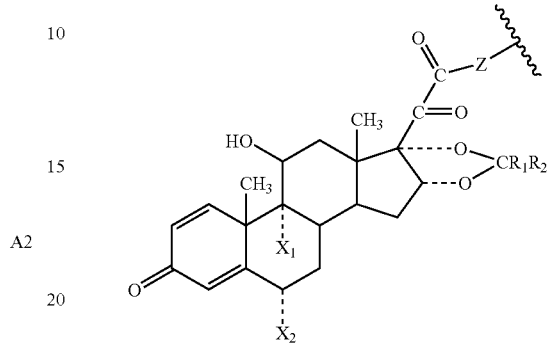

A4 or stereoisomeric forms thereof, wherein the 1,2-position represents a saturated or unsaturated double bond, wherein Z is oxygen or a NH group, $R_1$ is hydrogen, a straight or branched hydrocarbon chain having 1-4 carbon atoms, $R_2$ is hydrogen, a straight or branched hydrocarbon chain having 1-10 carbon atoms with the proviso that $R_1$ and $R_2$ are not simultaneously hydrogen, $X_1$ is hydrogen or halogen, $X_2$ is hydrogen or halogen, with halogen meaning fluorine, chlorine or bromine;

A5 or stereoisomeric forms thereof, wherein the 1,2-position represents a saturated or unsaturated double bond, $R_1$ is hydrogen, a straight or branched hydrocarbon chain having 1-4 carbon atoms, $R_2$ is hydrogen, a straight or branched hydrocarbon chain having 1-10 carbon atoms with the proviso that $R_1$ and $R_2$ are not simultaneously hydrogen, $X_1$ is hydrogen or halogen, $X_2$ is hydrogen or halogen, with halogen meaning fluorine, chlorine or bromine, preferably fluorine;

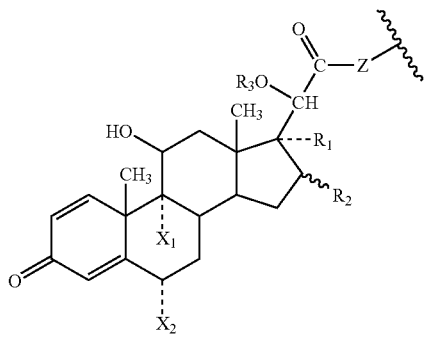

A6 wherein Z is oxygen or a NH group, $R_1$ is hydrogen or a hydroxyl group with a free hydrogen or a hydroxyl group or O-acyl or O-alkyl group, $R_2$ is hydrogen or a methyl group, which may be oriented in α- or β-position, $R_3$ is hydrogen or a radical of an acid having 1-4 carbon atoms, $X_1$ is hydrogen or halogen, $X_2$ is hydrogen or halogen, with halogen meaning fluorine, chlorine or bromine, preferably fluorine, 1,2-position may represent a double or single carbon-carbon bond, and L is a chain with the formula —$CR_1R_2(CR_3R_4)_n CR_5R_6$—, wherein $R_1, R_2, R_3, R_4, R_5, R_6$ may be hydrogen, $C_1$-$C_4$-alkyl, aryl, metoxy, halogen, hydroxy or mercapto groups, wherein n is 1-10, and one or more —$CR_3R_4$— groups may be substituted with oxygen, sulphur, an aromatic nucleus or an amino group additionally bearing hydrogen or a $C_1$-$C_4$ alkyl or aryl group, or $R_1, R_2, R_3, R_4, R_5, R_6$ may also together form one or more double or triple bonds in a chain, thus forming alkenyl or alkinyl, with the proviso that at least one methylene group is situated at the end of linking L group.

The chain covalently links subunits M and A via functional groups such as amides, ureates, carbamates, ethers, esters or via alkyl-alkyl or carbon-carbon bonds.

The terms used in the present invention are defined as stated hereinafter if not specified otherwise.

"Alkyl" means a monovalent alkane (hydrocarbon), wherefrom a radical is derived, which may be a straight-chain one, a branched-chain one, a cyclic one or a combination of straight-chain and cyclic hydrocarbons and branched-chain and cyclic hydrocarbons. Preferred straight-chain or branched-chain alkyls include methyl, ethyl, propyl, iso-propyl, butyl, sec-butyl and t-butyl groups. Preferable cycloalkyls include cyclopentyl and cyclohexyl groups. Alkyl also represents both a straight-chain or a branched-chain allyl group including or being interrupted by a cycloallyl portion.

"Alkenyl" means a hydrocarbon radical, which is a straight-chain one, a branched-chain one, a cyclic one or a combination of straight-chain and cyclic hydrocarbons and branched-chain and cyclic hydrocarbons and comprises at least one double carbon-carbon bond. Mainly ethenyl, propenyl, butenyl and cyclohexenyl groups are meant thereby. As already mentioned above for "alkyls", also alkenyls may be straight-chain, branched-chain or cyclic ones, where a part of the alkenyl group may include double bonds and may also be substituted when a substituted alkenyl group is in question. Alkenyl also represents both a straight-chain or a branched-chain alkenyl group including or being interrupted by a cycloalkenyl portion.

"Alkynyl" means a hydrocarbon radical, which is a straight-chain or a branched-chain one and includes at least one and at most three triple carbon-carbon bonds. Mainly ethynyl, propynyl and butynyl groups are meant thereby.

"Aryl" means an aromatic ring such as phenyl group, substituted phenyl or similar groups as well as rings that are fused such as naphtyl and the like. Aryl includes at least one ring having at least 6 carbon atoms or two rings having together 10 carbon atoms, possessing alternating double (resonance) bonds between carbon atoms (mainly phenyl and naphtyl rings). Aryl groups may be additionally substituted with one or two substituents, which may be halogen (fluorine, chlorine or bromine) and hydroxy, $C_1$-$C_7$ alkyl, $C_1$-$C_7$ alkoxy or aryloxy, $C_1$-$C_7$ alkylthio or arylthio, alkylsulfonyl, ciano or amino groups.

A further object of the present invention relates to a process for the preparation of compounds represented by the structure I.

These compounds can be prepared from the corresponding steroid part represented by the general structures A1 to A6, wherein all radicals and symbols have the meanings as defined for substructures A1 to A6, and macrolide intermediates represented by the general structures M1 to M6 by linking them via appropriate functional L groups. In an analogous manner, it is also possible to prepare compounds represented by the structure I with nonsteroid anti-inflammatory subunits via their free functionalities suitable for linkage.

From carboxylic acids of steroid subunits represented by the structures A1 to A4 and A6, which are prepared as described in the literature (Suzuki, T. et al, *Chem. Soc., Perkin Trans.* 1 1998, 3831-3836), (McLean, H. M. et al, *J. Pharm. Sci.* 1994, 83, 476-480), (Little, R. J. et al, *Pharin. Res.* 1999, 16, 961-967), (Kertesz D. J. et al, *J. Org. Chem.* 1986, 51, 2315-2328), (Bodor N. S. U.S. Pat. No. 4,710,495, 1987), a compound of the general formula I can be prepared, where the activation with carboxydiimide and benzotriazole (HOBT) in anhydrous dichloromethane in the presence of a base such as triethylamine at room temperature in a flow of argon is used for the formation of an amide bond (Scheme 1)

Scheme 1

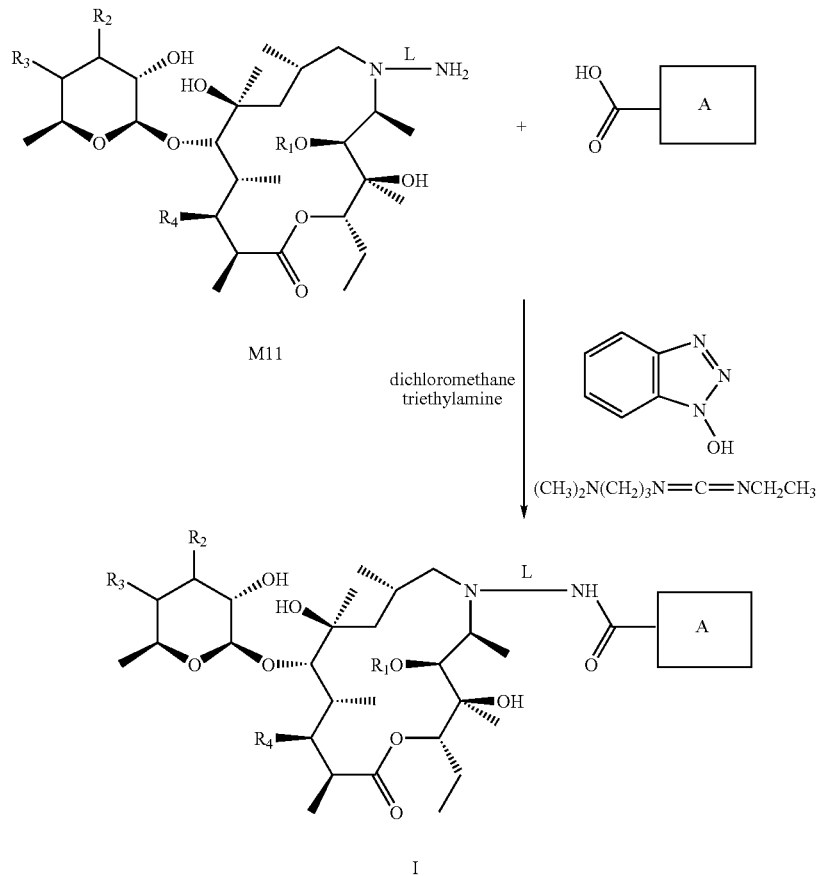

When the linking of macrolide subunits to the steroid subunits takes place via an ester bond, the synthesis is performed via the macrolide intermediate M7.

lamine and dimethylaminopyridine (DMAP), thus forming intermediates M7 for linking with carboxylic acids of the subunit A (Scheme 2).

Scheme 2

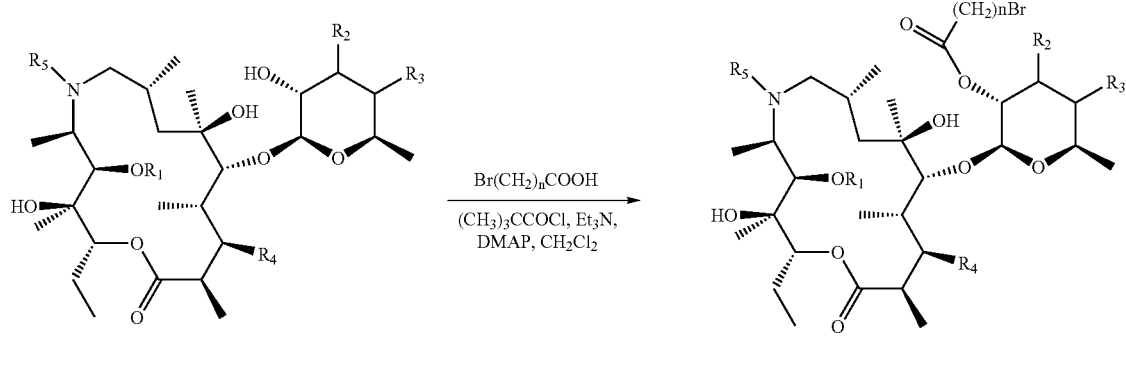

Esterification in position 2' of the macrolide can be performed by the reaction with a halogen-substituted acid in dry dichloromethane in the presence of pivaloyl chloride, triethylamine Such an intermediate can further react with the carboxylic functionality of subunit A in case of a steroid subunit such as represented by the structures A1 to A4 and A6.

The reaction is performed in dry DMF in the presence of a base such as potassium carbonate (K$_2$CO$_3$) in a flow of argon, yielding a potassium salt of the acid, which in the reaction with the macrolide intermediate gives a compound I of the present invention (Scheme 3).

When the macrolide subunit means M2 (a macrolide free of cladinose in position 3), it is also possible to perform the coupling with an anti-inflammatory subunit A via an ester bond, whereat the preparation of intermediates M8 and M9 is necessary (Scheme 4).

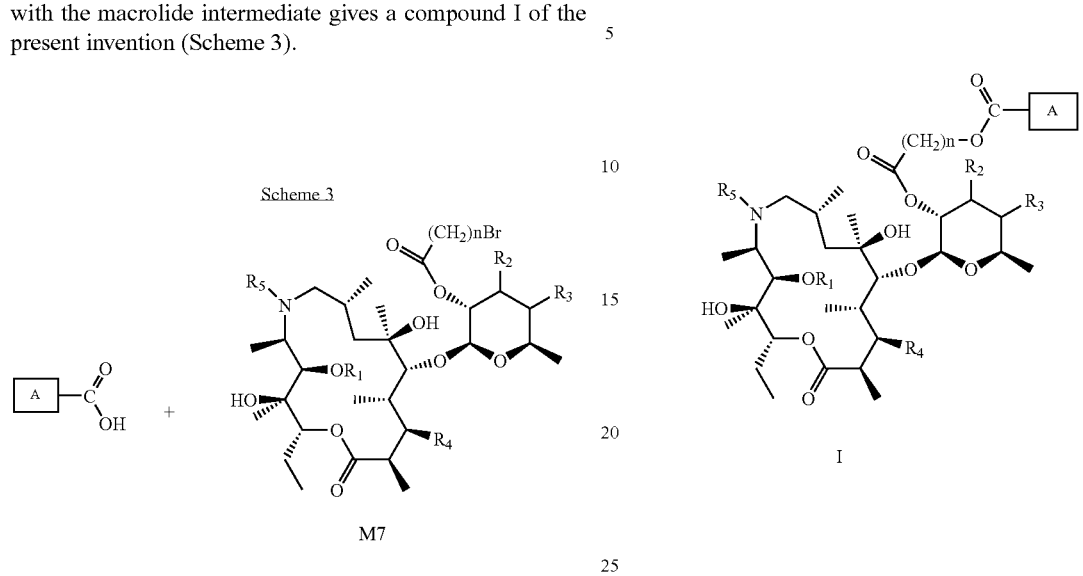

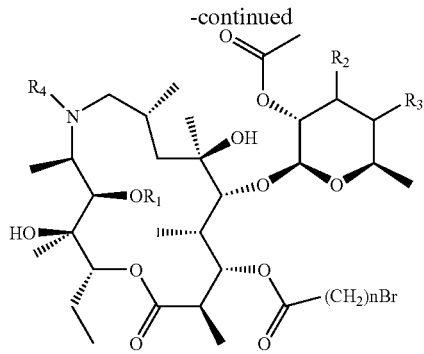
M9
Esterification with the carboxylic group of subunit A occurs selectively due to the protected 2' hydroxyl group of macrolide M9, which is also reactive.
Scheme 5
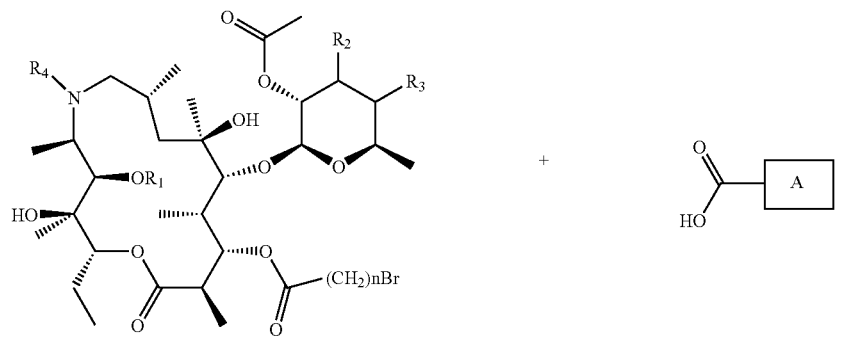
M9
$$\downarrow \begin{array}{c} K_2CO_3 \\ DMF \end{array}$$
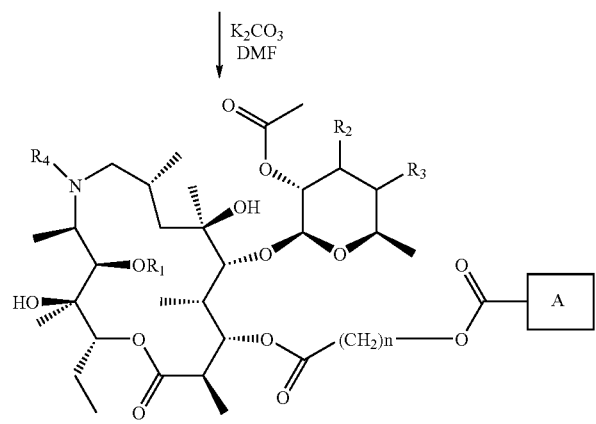
I The synthesis of a compound of the structure I from a macrolide subunit indicated by M1 is performed from an intermediate, whose synthesis is described in Agouridas C., *J. Med. Chem.* 1998, 41, 4080-4100, in the manner and by the use of reagents described therein. From said intermediate M10 a compound of the structure I is synthesized by the reaction with an anti-inflammatory subunit A bearing a carboxylic functionality by the use of potassium carbonate in dry DMF at room temperature (Scheme 6).

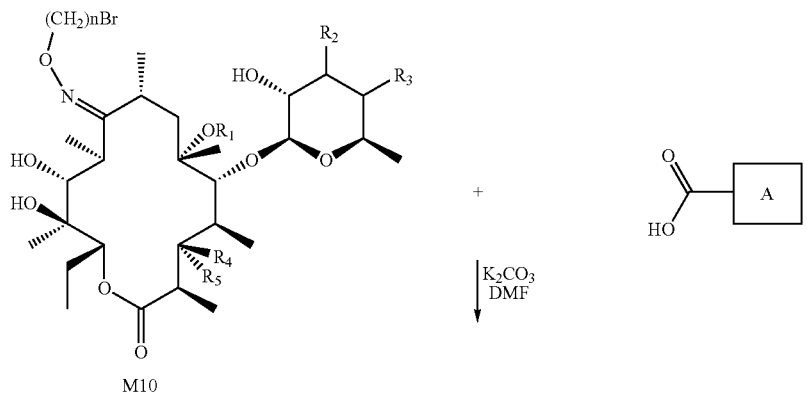

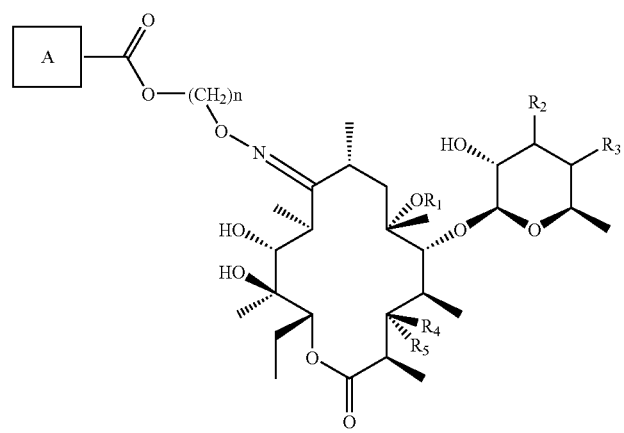

The compounds of the general structure I comprising a compound M3 as the macrolide unit are synthesized by linking a modified anti-inflammatory unit A8 with a macrolide M3, which is prepared according to the already mentioned method (Agouridas C., *J. Med. Chem.* 1998, 41, 4080-4100). The anti-inflammatory intermediate A8 is prepared from an acid of the anti-inflammatory compound and a corresponding protected diamine (Boc-protection only from one side) in the presence of hidroxybenzotriazole and EDC in a suitable solvent, preferably dichloromethane or DMF. After obtaining the corresponding amide A7, a deprotection of the terminal amino group is performed by the use of TFA in dichloromethane at room temperature (Scheme 7).

Scheme 7

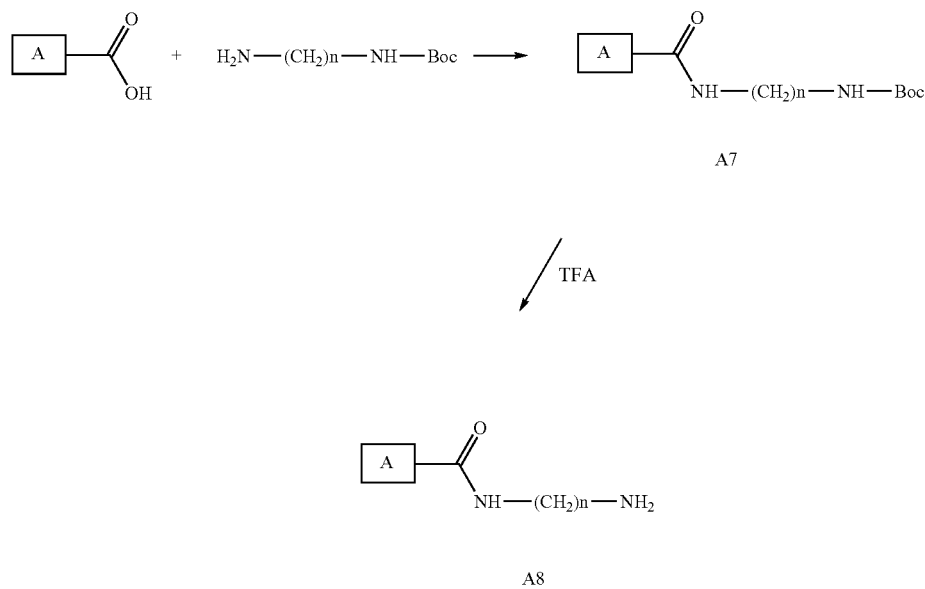

The intermediate obtained according to the Scheme 7 is reacted in acetonitrile in a flow of nitrogen with a macrolide subunit M12, which is activated by carboxydiimide and comprises protected hydroxyl groups in positions 2' 4" (Scheme 8).

Scheme 8

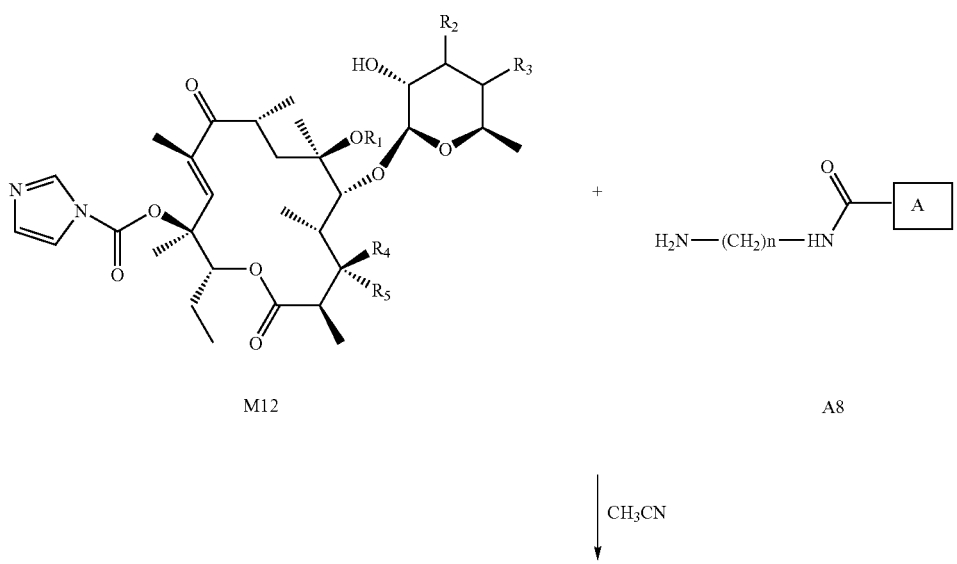

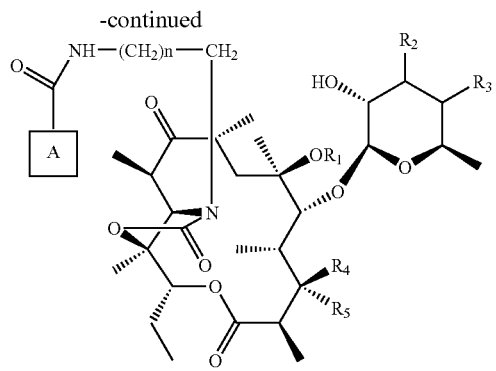

I

If the steroid subunit is described as indicated for the general structure A5, wherein all groups and radicals have the meanings as described in the above-mentioned definitions, the coupling reaction with the macrolide group is performed by the esterification of the intermediate A9 obtained according to the literature (HU 55409) and of the macrolide hydroxyl group (Scheme 9).

Scheme 9

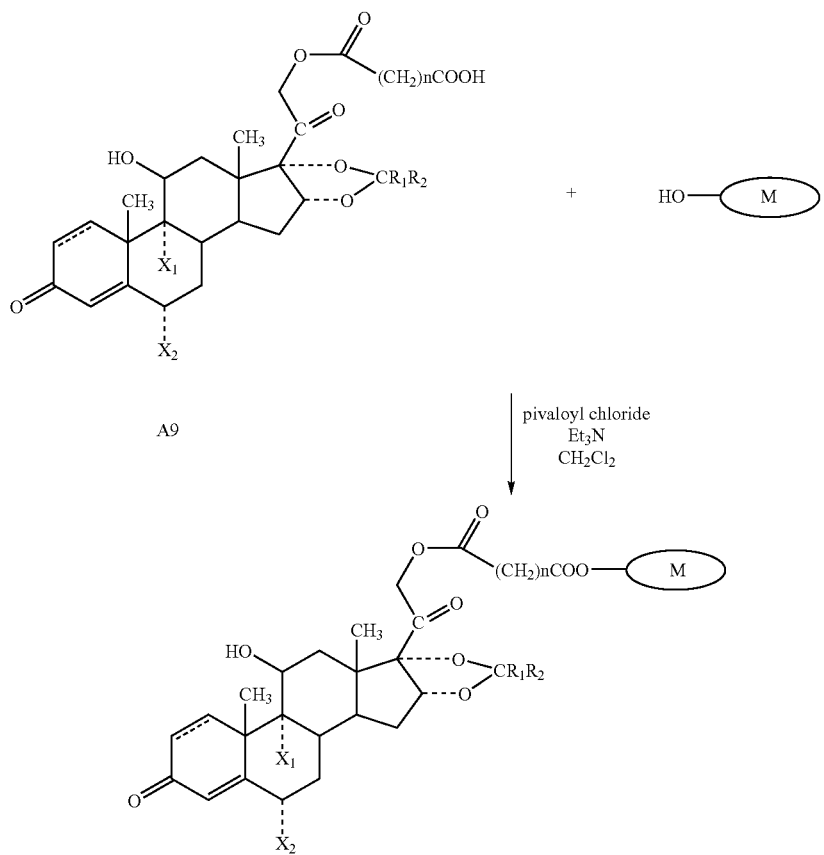

I

A further object of the present invention relates to the use of compounds of the general structure I as anti-inflammatory, anti-anaphylactic and immunomodulating agents, which, depending on the inflammation site, can be administered in different ways such as percutaneously, orally, buccally, rectally, parenterally or by inhalation when a topical application within the respiratory tract is intended.

A further object of the present invention relates to the preparation of such pharmaceutical forms of compounds to achieve the optimal bioavailability of the active compound I. For percutaneous administration the compound I can be prepared in a form of an ointment or a cream, a gel or a lotion. Ointments, creams and gels can be formulated by the use of a water or oil base under the addition of an appropriate emulgator or gelling agent, when a gel form is formulated. The formulation is especially significant for respiratory inhalation, wherein the compound I can be in the form of an aerosol under pressure. For all forms of aerosol formulations it is recommended to micronise the compound I, which has been previously homogenised in lactose, glucose, higher fatty acids, sodium salt of dioctylsulfosuccinic acid or, most preferably, in carboxymethyl cellulose, in order to achieve the size of 5 μm for the greatest number of particles. For the inhalation formulation the aerosol can be mixed with a propellant serving for spraying the active substance.

The compound I for inhalation application can be applied in the form of a dry powder with micronised particles.

The compound can also be incorporated in a formulation for treating Crohn's disease, where it can be administered orally or rectally. The formulation for oral administration must be formulated so as to enable the bioavailability of the compound in the inflammation part of the intestine. This can be achieved by different combinationa of delayed release formulations. The compound I can also be used in the treatment of Crohn's disease and intestine inflammation disease if the compound is applied in the form of a clyster, wherefor a suitable formulation can be used.

The appropriate preparations of the compounds that are the object of the present invention can be used in the prophylaxis or treatment of different diseases and pathological inflammatory conditions including asthma, chronic obstructive pulmonary disease, inflammatory nasal diseases such as allergic rhinitis, nasal polyps, intestinal diseases such as Crohn's disease, colitis, intestine inflammation, ulcerative colitis, dermatological inflammations such as eczema, psoriasis, allergic dermatitis, neurodermnatitis, pruritus, conjunctivitis and rheumatoid arthritis.

The therapeutic effect of the compounds of the present invention was determined in the following in vitro and in vivo experiments.

Assay of Binding to the Human Glucocorticoid Receptor

The gene for alpha isoform of human glucocorticoid receptor was cloned by reverse polymerase chain reaction. The total RNA was isolated from human peripheral blood lymphocites according to the instructions of the manufacturer (Qiagen), transcripted into cDNA with AMV reverse transcriptase (Roche) and the gene was multiplied by specific primers

```
1)  5' ATATGGATCCCTGATGGACTCCAAAGAATCATTAACTCC3'

2)  5' ATATCTCGAGGGCAGTCACTTTTGATGAAACAGAAG3'
```

The obtained reaction product was cloned into XhoI/BamHI site of Bluescript KS plasmid (Stratagene), subjected to sequencing by dideoxy fluorescent method with M13 and M13 rev primers (Mycrosynth) and then it was cloned into XhoI/BamHI site of pcDNA3.1 rhygro(+)plasmid (Invitrogen). $1 \times 10^5$ COS-1 cells were seeded onto a 12-well plate (Falcon) in DMEM medium (Life Technologies) with 10% FBS (Biowhitaker) and cultivated up to a 70% confluence at 37° C. in an atmosphere with 5% $CO_2$. The medium was removed and 1 μg of DNA, 7 μl of PLUS reagent and 2 μl of Lipofectamine (Life Technologies) in 500 μl DMEM were added per well. The cells were incubated at 37° C. in an atmosphere with 5% $CO_2$ and after 5 hours the same volume of 20% FBS/DMEM was added. After 24 hours the medium was completely changed. 48 hours after the transfection, the test compounds in different concentrations and 24 nM [$^3$H] dexamethasone (Pharmacia) in DMEN medium were added. The cells were incubated for 90 minutes at 37° C. in an atmosphere with 5% $CO_2$, washed three times with PBS buffer (Sigma), cooled to 4° C. (pH=7.4) and then lyzed in Tris buffer (pH=8.0) (Sigma) with 0.2% SDS (Sigma). After the addition of UltimaGold XR (Packard) scintillation liquid, the residual radioactivity was read in a Tricarb (Packard) β-scintillation counter.

Compounds 9, 10 and 27 are able to compete with radioactive dexamethasone in the binding site on the glucocorticoid receptor.

Assay of Steroid Introduction into Cells

CHO and COS-1 cells were cultivated up to confluence in 75 $cm^2$ flasks in Hamm F 12 medium (Life Technologies) with 10% FBS (CHO) or in DMEM medium with 10% FBS (COS-1). 1 μM of radioactive compound 10 with total 2 μCi activity was added onto the cells and it was incubated for 90 minutes at 37° C. in an atmosphere with 5% $CO_2$. The cell supernatant was collected, the cells were lysed and then the radioactivity in the cell lysate as well as in the cell supernatant was read. The compound 10 was able to accumulate in the cells in a greater concentration than in the supernatant.

Assay of Inhibition of Mouse T-Cell hybridoma 13 Proliferation as a Result of apoptose Induction In a 96-well plate triplicates of test steroid dilution in RPMI medium (Imunoloski zavod) with 10% PBS were performed. To the solutions of compounds 20 000 cells per well were added and incubated overnight at 37° C. in an atmosphere with 5% $CO_2$, then 1 μCi of [$^3$H] thymidine (Pharmacia) was added and it was incubated for additional 3 hours. The cells were harvested by sucking over GF/C filter (Packard). Onto each well 30 μl of Microscynt O scintillation liquid (Packard) were added and the incorporated radioactivity was measured on a β-scintillation counter (Packard). The specifity of apoptose induction by glucocorticoids was proven by antagonising the proliferation inhibition with mifepristone (Sigma).

Compounds 8, 9, 10 and 27 demonstrated an inhibition of cell hybridoma 13 proliferation.

Assay of Inhibition of Interleukin-2 Production

Onto a 96-well plate (Nunc) 15 ng of 2C11 antibodies (Pharmingen) per well were added and left to adsorb in PBS buffer (pH=7.4) overnight at 4° C. PBS was removed, the plate was washed with RPMI medium and then 50 000 cells per well were added and incubated in the medium with and without a dilution of the test compounds. The concentration of IL-2 in the supernatant was measured by ELISA specific for mouse IL-2 (R&D Systems).

The compounds 9, 10 and 27 demonstrate an inhibition of interleukin-2 production induced by the stimulation via CD3 receptor.

TABLE 2

| Compound | Binding to the glucocorticoid receptor | Induction of H13 cells apoptose | Inhibition of IL-2 synthesis |
|---|---|---|---|
| 5 | ND | − | − |
| 8 | + | + | + |
| 9 | + | + | + |
| 10 | + | + | + |
| 11 | ND | − | − |
| 27 | + | + | + |
| dexamethasone | + | + | + |

ND—not determined

Model of Croton Oil-Induced Ear Edema

Male Sprague Dawley rats with body weight of 200-250 g were randomly divided into groups, marked and the inital ear thickness was measured with a digital caliper.

To the control group 50 μl of solvent (acetone, Kemika) per ear were applied. In the same manner also the test compound in a dose of 1 mg/ear or the standard (1 mg/ear of dexamethasone, Krka) dissolved in acetone were applied. Thirty minutes later an ear edema was induced with 20% croton oil (Sigma). The maximum intensity of the inflammation was reached five hours after the application of croton oil. The percentage of the ear edema inhibition was determined by comparing the ears of the treated animals and of the control ones. In this model the compound 10 was tested, which demonstrated a similar activity as the tested standard.

Model of Lung Eosinophilia in Mice

Male Balb/C mice with a body weight of 20-25 g were randomly divided into groups. They were sensibilized by an i.p. injection of ovalbumine (OVA, Sigma) on zero day and on the fourteenth day. On the twentieth day the mice were subjected to a provocative test by i.n. application of OVA (positive control or test groups) or PBS (negative control). 48 hours after i.n. aplication of OVA, the animals were anesthetized and the lungs were rinsed with 1 ml of PBS. The cells were separated on Cytospin 3 cytocentrifuge (Shandon). The cells were stained in Diff-Quick (Dade) and the percentage of eozinophiles was determined by differential counting of at least 100 cells.

Fluticasone and beclomethasone were used as standard substances under positive and negative control.

The compounds were administered daily i.n. or i.p. in different doses 2 days before provocative test and up to the completion of the test.

Compounds 8, 9 and 10 statistically significantly (t-test, $p<0.05$) reduced the number of eosinophiles in the lung rinse with regard to the positive control.

Influence of Compounds on the Thymus Weight

Male Sprague Dawley rats with a body weight of 200 g were randomly divided into groups of six animals. To anaesthetized animals sterilized weighed pellets of filter paper were implanted s.c. dorsally. The pellets in the control group were impregnated with acetone, whereas in the test groups they were impregnated either with the standard (prednisolone, Sigma) or with the compound 10. After 7 days the animals were put to sleep and their thymuses were isolated and weighed. The systemic effects were estimated by comparing the thymus weight in the test and control groups.

The standard statistically significantly reduced the thymus weights with regard to the control, while the compound 10 did not affect the thymus weights.

PREPARATION PROCESSES WITH EXAMPLES

The present invention is illustrated but in no way limited by the following Examples.

EXAMPLE 1

Intermediate M11, Wherein $R_4$ Represents a Cladinose Group (9-deoxo-9a-aza-9a-(γ-aminopropyl)-9a-homoerythromycin A)

To a solution of 9-deoxo-9a-aza-9a-(β-cianoethyl)-9a-homoerythromycin A (3 g; 3.8 mmole) in ethanol (100 ml), 500 mg of $PtO_2$ were added. The reaction was performed in an autoclave during 2 days under the pressure of 40 bar. Subsequently, the reaction mixture was filtered and ethanol was evaporated on a rotary evaporator. The residue was purified on a silica gel column (eluant: $CH_3OH:CH_2Cl_2:NH_4OH=50:30:2$). 700 mg of the pure product were obtained. $MS(ES^+)$: 793 $(MH^+)$ Intermediate M11, Wherein $R_4$ Represents a Hydroxyl Group The intermediate M11 was prepared according to the process described in Example 1 from 3-decladinosyl-9-deoxo-9a-aza-9a(β-cianoethyl)-9a-homoerythromycin A (3.5 g; 5.55 mmole). 985 mg of the product were obtained. $MS(ES^+)$: 635 $(MH^+)$

EXAMPLE 2

Intermediate M7, Wherein $R_4$ Represents a Cladinose Group

To a solution of 5-bromovaleric acid (1.282 g; 7.07 mmole) in dry $CH_2Cl_2$ (10 ml), 1 ml (7.23 mmole) of triethylamine, 868 mg (7.10 mmole) of 4-dimethyl-aminopyridine and 0.940 ml (7.63 mmole) of pivaloyl chloride were added. The solution was stirred for 2 hours at room temperature in a flow of argon and then a solution of azithromycin (2 g; 2.67 mmole) in 10 ml of dry $CH_2Cl_2$ was added. The reaction mixture was stirred for three days at room temperature. Subsequently, 60 ml of saturated $NaHCO_3$ solution were added to the reaction mixture and the layers were separated. The aqueous layer was twice more extracted with 40 ml of $CH_2Cl_2$. The combined organic extracts were washed with a saturated NaCl solution, dried over $K_2CO_3$ and evaporated in a rotary evaporator. The obtained oily product was purified on a silica gel column (eluant: $CH_2Cl_2:CH_3OH:NH_4OH=90:9:1.5$). 511 mg of the pure product were obtained. $MS(ES^+)$: 912 $(MH^+)$ The intermediates M7 and M9 were prepared according to the process described in Example 2.

Intermediate M7, Wherein $R_4$ Represents a Hydroxyl Group

The intermediate M7 was prepared from 3-decladynosyl azithromycin (1 g; 1.71 mmole) and 5-bromovaleric acid (929 mg; 5.13 mmole). 400 mg of the product were obtained. $MS(ES^+)$: 754 $(MH^+)$ Intermediate M9

The intermediate M9 was prepared from 2'-acetyl-3-decladynosyl azithromycin (1.1 g; 1.70 mmole) and 5-bromovaleric acid (921 mg; 5.09 mmole). 329 mg of the product were obtained. MS(ES⁺): 795 (MH⁺)

EXAMPLE 3

Compound 1

To a suspension of 9α-chloro-6α-fluoro-11β,17α-dihydroxy-16α-methyl-3-oxoandrosta-1,4-diene-17β-carboxylic acid (100 mg; 0.29 mmole) in dry CH₂Cl₂ (5 ml) cooled to 0° C. under argon, 0.380 ml (2.73 mmole) of triethylamine, 80 mg (0.59 mmole) of 1-hydroxybenzotriazole, 230 mg (0.29 mmole) of 9-deoxo-9a-aza-9a-(γ-aminopropyl)-9a-homoerythromycin A and 235 mg (1.23 mmole) of 1-(3-dimethylaminopropyl)-3-ethyl-carbodiimide hydrochloride were added. The reaction mixture was stirred for 24 hours at room temperature in a flow of argon, then evaporated to a smaller volume on a rotary evaporator and purified on a silica gel column. (eluant: CHCl₃:CH₃OH:NH₄OH=6:1:0.1). 224 mg of white crystals were obtained (Table 1).

Compounds 2-12 were prepared from 9-deoxo-9a-aza-9a-(γ-aminopropyl)-9a-homoerythromycin A and the corresponding steroid acids according to the process described in Example 3 and stated in Table 1.

Compound 2

By a reaction of 9-deoxo-9a-aza-9a-(γ-aminopropyl)-9a-homoerythromycin A (230 mg; 0.29 mmole) and 11β,17α-dihydroxyandrosta-1,4-diene-3-one-17β-carboxylic acid (100 mg; 0.29 mmole), white crystals (285 mg) were obtained.

Compound 3

By a reaction of 9-deoxo-9a-aza-9a-(γ-aminopropyl)-9a-homoerythromycin A (197 mg; 0.25 mmole) and 11β-hydroxy-17α-metoxyandrost-4-ene-3-one-17β-carboxylic acid (90 mg; 0.25 mmole), white crystals (115 mg) were obtained.

Compound 4

By a reaction of 9-deoxo-9a-aza-9a-(γ-aminopropyl)-9a-homoerythromycin A (174 mg; 0.22 mmole) and 9α-fluoro-11β-hydroxy-16α-methyl-androsta-1,4-diene-3-one-17β-carboxylic acid (80 mg; 0.22 mmole), white crystals (224 mg) were obtained.

Compound 5

By a reaction of 9-deoxo-9a-aza-9a-(γ-aminopropyl)-9a-homoerythromycin A (230 mg; 0.29 mmole) and 11β-hydroxyandrost-4-ene-3-one-17β-carboxylic acid (96 mg; 0.29 mmole), white crystals (238 mg) were obtained.

Compound 6

By a reaction of 9-deoxo-9a-aza-9a-(γ-aminopropyl)-9a-homoerythromycin A (230 mg; 0.29 mmole) and 9α-fluoro-11β,17α-dihydroxyandrosta-1,4-diene-3-one-17β-carboxylic acid (106 mg; 0.29 mmole), white crystals (225 mg) were obtained.

Compound 7

By a reaction of 9-deoxo-9a-aza-9a-(γ-aminopropyl)-9a-homoerythromycin A (230 mg; 0.29 mmole) and 6α-fluoro-11β,17α-dihydroxy-16α-methyl-androsta-1,4-diene-3-one-17β-carboxylic acid (110 mg; 0.29 mmole), white crystals (107 mg) were obtained.

Compound 8

By a reaction of 9-deoxo-9a-aza-9a-(γ-aminopropyl)-9a-homoerythromycin A (230 mg; 0.29 mmole) and 11β,17α-dihydroxyandrost-4-ene-3-one-17β-carboxylic acid (100 mg; 0.29 mmole), white crystals (75 mg) were obtained.

Compound 9

By a reaction of 9-deoxo-9a-aza-9a-(γ-aminopropyl)-9a-homoerythromycin A (230 mg; 0.29 mmole) and 6α,9α-difluoro-11β,17α-dihydroxy-16α-methylandrosta-1,4-diene-3-one-17β-carboxylic acid (115 mg; 0.29 mmole), white crystals (258 mg) were obtained.

Compound 10

By a reaction of 9-deoxo-9a-aza-9a-(γ-aminopropyl)-9a-homoerythromycin A (230 mg; 0.29 mmole) and 9α-fluoro-11β,17α-dihydroxy-16α-methylandrosta-1,4-diene-3-one-17β-carboxylic acid (110 mg; 0.29 mmole), white crystals (224 mg) were obtained.

Compound 11

By a reaction of 9-deoxo-9a-aza-9a-(γ-aminopropyl)-9a-homoerythromycin A (197 mg; 0.24 mmole) and 9α-chloro-11β,17α-dihydroxy-16α-methylandrosta-1,4-diene-3-one-17β-carboxylic acid (96 mg; 0.24 mmole), white crystals (170 mg) were obtained.

Compound 12

By a reaction of 9-deoxo-9a-aza-9a-(γ-aminopropyl)-9a-homoerythromycin A (230 mg; 0.29 mmole) and 17α-hydroxyandrost-4-ene-3,11-dione-17β-carboxylic acid (100 mg; 0.29 mmole), white crystals (247 mg) were obtained.

EXAMPLE 4

Compound 13

A mixture of 6α,9α-difluoro-11β,17α-trihydroxy-3-oxoandrosta-1,4-diene-17β-carboxylic acid-16,17-acetonide (104 mg; 0.24 mmole), diizopropylethylamine (45 ml, 0.26 mmole), 1-hidroxybenzotriazole (65 mg; 0.48 mmole), 9-deoxo-9a-aza-9a-(γ-aminopropyl)-9a-homoerythromycin A (190 mg; 0.24 mmole) and 1-(3-dimethyl-aminopropyl)-3-ethyl-carbodiimide hydrochloride (184 mg; 0.96 mmole) in dry DMF (10 ml) was heated under reflux while stirring at 100° C. in an argon atmosphere. Subsequently, the reaction mixture was cooled and evaporated on a rotary evaporator. The residue was purified on a silica gel column (eluant: CHCl₃:CH₃OH:NH₄OH=6:1:0.1). 31 mg of the pure product were obtained (Table 1).

Compound 14

Compound 14 was prepared according to the process described in Example 4 from 6α,9α-difluoro-11β,16α,17α-trihydroxy-3-oxoandrosta-1,4-diene-17β-carboxylic acid-16,17-acetonide (104 mg; 0.24 mmole) and 3-decladinosyl-

EXAMPLE 5

Compound 15

To a suspension of 9α-chloro-6α-fluoro-11β,17α-dihydroxy-16α-methyl-3-oxoandrosta-1,4-diene-17β-carboxylic acid (110 mg; 0.27 mmole) in dry $CH_2Cl_2$ (5 ml) cooled to 0° C. in a flow of argon, 0.348 ml (2.5 mmole) of triethylamine, 73 mg (0.54 mmole) of 1-hydroxybenzotriazole, 169 mg (0.27 mmole) of 3-decladinosyl-9-deoxo-9a-aza-9a-(-(γ-aminopropyl)-9a-homoerythromycin A and 215 mg (1.12 mmole) of 1-(3-dimethylaminopropyl)-3-ethyl-carbodiimide hydrochloride were added. The reaction mixture was stirred for 24 hours at room temperature, evaporated to a smaller volume on a rotary evaporator and purified on a silica gel column (eluant: $CHCl_3:CH_3OH:NH_4OH=6:1:0.1$). 235 mg of white crystals were obtained (Table 1).

Compounds 16-19 were prepared according to the process described in Example 5 and stated in Table 1.

Compound 16

By a reaction of 6α-fluoro-11β,17α-dihydroxy-16α-methyl-3-oxoandrosta-1,4-diene-17β-carboxylic acid (90 mg; 0.24 mmole) and 3-decladinosyl-9-deoxo-9a-aza-9a-(-(γ-aminopropyl)-9a-homoerythromycin A (150 mg; 0.24 mmole), white crystals (138 mg) were obtained.

Compound 17

By a reaction of 6α,9α-difluoro-11β,17α-dihydroxy-16α-methyl-3-oxoandrosta-1,4-diene-17β-carboxylic acid (94 mg; 0.24 mmole) and 3-decladinosyl-9-deoxo-9a-aza-9a-(-(γ-aminopropyl)-9a-homoerythromycin A (150 mg; 0.24 mmole), white crystals (163 mg) were obtained.

Compound 18

By a reaction of 11β,17α-dihydroxyandrost-4-ene-3-one-17β-carboxylic acid (84 mg; 0.24 mmole) and 3-decladinosyl-9-deoxo-9a-aza-9a-(-(γ-aminopropyl)-9a-homo-erythromycin A (150 mg; 0.24 mmole), white crystals (112 mg) were obtained.

Compound 19

By a reaction of 9α-fluoro-11β,17α-dihydroxy-16α-methyl-3-oxoandrosta-1,4-diene-17β-carboxylic acid (110 mg; 0.29 mmole) and 3-decladinosyl-9-deoxo-9a-aza-9a-(-(γ-aminopropyl)-9a-homoerythromycin A (185 mg; 0.29 mmole), white crystals (155 mg) were obtained.

EXAMPLE 6

Compound 20

To a suspension of stereoisomeric acid (20 R,S)-11β,17,20-trihydroxy-3-oxoandrosta-1,4-diene-21-carboxylic acid (200 mg; 0.53 mmole) in dry $CH_2Cl_2$ (5 ml) under argon, 0.760 ml of triethylamine, 160 mg (1.2 mmole) of 1-hydroxybenzotriazole, 460 mg (0.58 mmole) of 9-deoxo-9a-aza-9a-(γ-aminopropyl)-9a-homoerythromycin A and 470 mg (2.45 mmole) of 1-(3-dimethylaminopropyl)-3-ethyl-carbodiimide hydrochloride were added. The reaction mixture was stirred for 24 hours at room temperature, then evaporated to a smaller volume on a rotary evaporator and purified on a silica gel column (eluant: $CHCl_3:CH_3OH:NH_4OH=6:1:0.1$). 405 mg of the product were obtained (Table 1).

EXAMPLE 7

Compound 21

To a solution of 9α-fluoro-11β,17α-dihydroxy-16α-methyl-3-oxoandrosta-1,4-diene-17β-carboxylic acid (135 mg; 0.35 mmole) in dry DMF (3 ml), potassium carbonate (49 mg; 0.35 mmole) was added. The reaction mixture was stirred at 0° C. in a flow of argon and then a solution of 311 mg (0.39 mmole) of the intermediate M9 in 4 ml of dry DMF was added. After stirring for 5 days at room temperature, DMF was evaporated on a rotary evaporator and the residue was purified on a silica gel column (eluant: $CHCl_3:CH_3OH:NH_4OH=10:1:0.1$). 53 mg of the pure product were obtained (Table 1).

EXAMPLE 8

Compound 22

To a solution of 6α,9α-difluoro-11β,17α-dihydroxy-16α-methyl-3-oxoandrosta-1,4-diene-17β-carboxylic acid (100 mg; 0.25 mmole) in dry DMF (3 ml), potassium carbonate (35 mg; 0.25 mmole) was added. The reaction mixture was stirred at 0° C. in a flow of argon and then a solution of 252 mg (0.28 mmole) of the intermediate M7, wherein $R_4$ represents cladinose, in 4 ml of dry DMF was added. After stirring for 2 days at room temperature, DMF was evaporated on a rotary evaporator and the residue was purified on a silica gel column (eluant: $CHCl_3:CH_3OH:NH_4OH=12:1:0.1$). 42 mg of the pure product were obtained (Table 1).

Compounds 23 and 24 were prepared according to the process described in Example 8 and stated in Table 1.

Compound 23

By a reaction of 9α-fluoro-11β,17α-dihydroxy-16α-methyl-3-oxoandrosta-1,4-diene-17β-carboxylic acid (99 mg; 0.26 mmole) and 285 mg (0.31 mmole) of intermediate M7, wherein $R_4$ represents cladinose, white crystals (42 mg) were obtained.

Compound 24

By a reaction of 9α-chloro-6α-fluoro-11β,17α-dihydroxy-16α-methyl-3-oxoandrosta-1,4-diene-17β-carboxylic acid (81 mg; 0.20 mmole) and 222 mg (0.24 mmole) of intermediate M7, wherein $R_4$ represents cladinose, white crystals (54 mg) were obtained (Table 1).

EXAMPLE 9

Compound 25

To a solution of 9α-fluoro-11β,17α-dihydroxy-16α-methyl-3-oxoandrosta-1,4-diene-17β-carboxylic acid (83 mg; 0.22 mmole) in dry DMF (3 ml), potassium carbonate (30 mg; 0.22 mmole) was added. The reaction mixture was stirred at 0° C. in a flow of argon and then a solution of 182 mg (0.24 mmole) of intermediate M7, wherein $R_4$ represents a hydroxyl group, in 4 ml of dry DMF was added. After stirring for 24 hours at room temperature, DMF was evaporated on a rotary evaporator and the residue was purified on a silica gel column (eluant: $CHCl_3:CH_3OH:NH_4OH=10:1:0.1$). 57 mg of the pure product were obtained.

Compounds 26 and 27 were prepared according to the process described in Example 9 and stated in Table 1.

Compound 26

By a reaction of 6α-fluoro-11β,17α-dihydroxy-16α-methyl-3-oxoandrosta-1,4-diene-17β-carboxylic acid (85 mg; 0.22 mmole) and 225 mg (0.25 mmole) of intermediate M7, wherein $R_4$ represents a hydroxyl group, white crystals (20 mg) were obtained.

Compound 27

By a reaction of 9α-chloro-6α-fluoro-11β,17α-dihydroxy-16α-methyl-3-oxoandrosta-1,4-diene-17β-carboxylic acid (100 mg; 0.24 mmole) and 200 mg (0.26 mmole) of intermediate M7, wherein $R_4$ represents a hydroxyl group, white crystals (59 mg) were obtained.

EXAMPLE 10

Compound 28

To a solution of 9α-fluoro-11β,17α-dihydroxy-16α-methyl-3-oxoandrosta-1,4-diene-17β-carboxylic acid (80 mg; 0.21 mmole) in dry DMF (3 ml), potassium carbonate (30 mg; 0.21 mmole) was added. The reaction mixture was stirred for one hour at room temperature in a flow of argon and then a solution of 163 mg (0.23 mmole) of 3-O-decladinosyl-6-O-methyl-3-oxoerythromycin-9-O-(2-bromoethyl)oxime in 3 ml of dry DMF was added. The reaction mixture was heated for 4 hours at 100° C. Then it was cooled to room temperature and 40 ml of ethyl-acetate and water (1:1) were added. The organic layer was separated, washed with water and dried over anhydrous potassium carbonate. The residue was purified on a silica gel column with a solvent system chlorophorm:methanol:ammonia=10:1:0.1. 160 mg of white crystals were obtained (Table 1).

TABLE 1

| Comp. | Structure | Molecular formula | M.p. (° C.) | MH+ (ES+) |
|---|---|---|---|---|
| 1 | 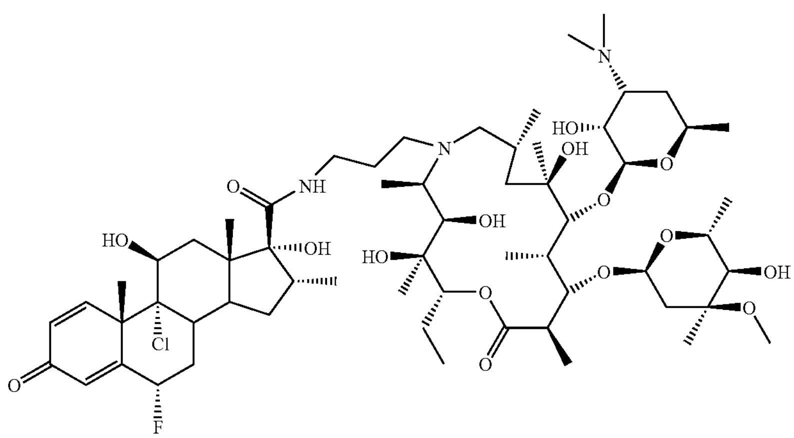 | $C_{61}H_{101}ClFN_3O_{16}$ | 194–202 | 1187 |
| 2 | 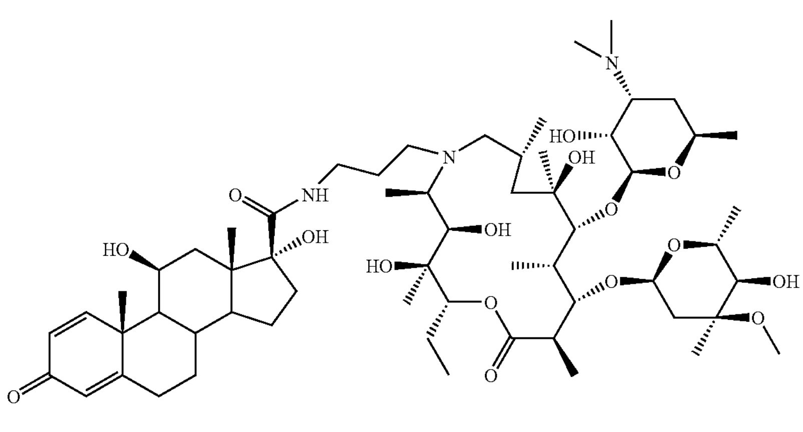 | $C_{60}H_{101}N_3O_{16}$ | | 1121 |

TABLE 1-continued

| Comp. | Structure | Molecular formula | M.p. (° C.) | MH+ (ES+) |
|---|---|---|---|---|
| 3 | 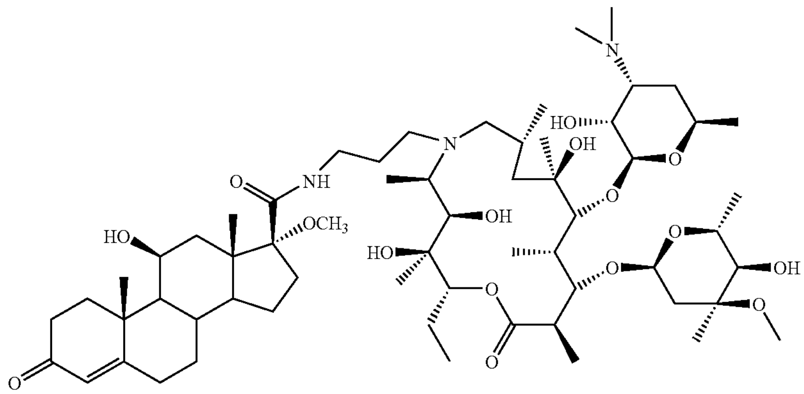 | $C_{61}H_{105}N_3O_{15}$ | — | 1137 |
| 4 | 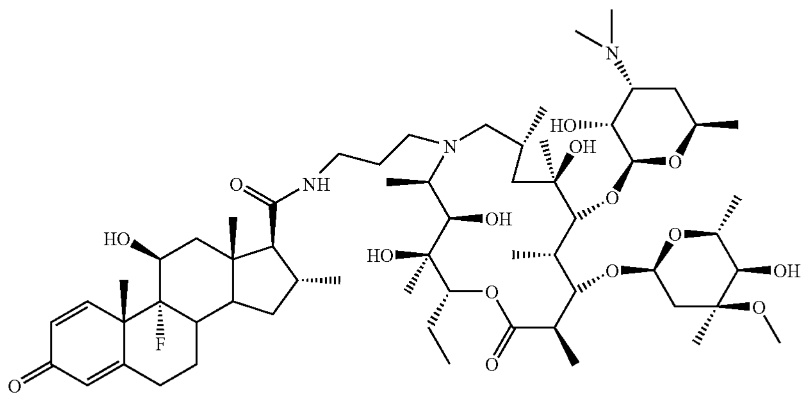 | $C_{61}H_{102}FN_3O_{15}$ | | 1137 |
| 5 | 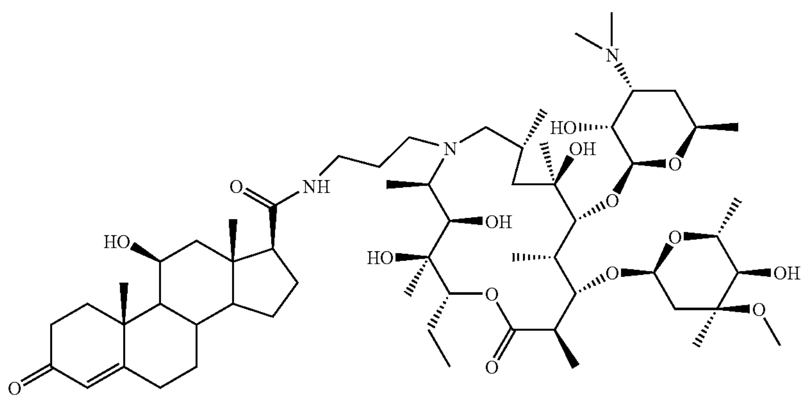 | $C_{60}H_{103}N_3O_{15}$ | — | 1106 |
| 6 | 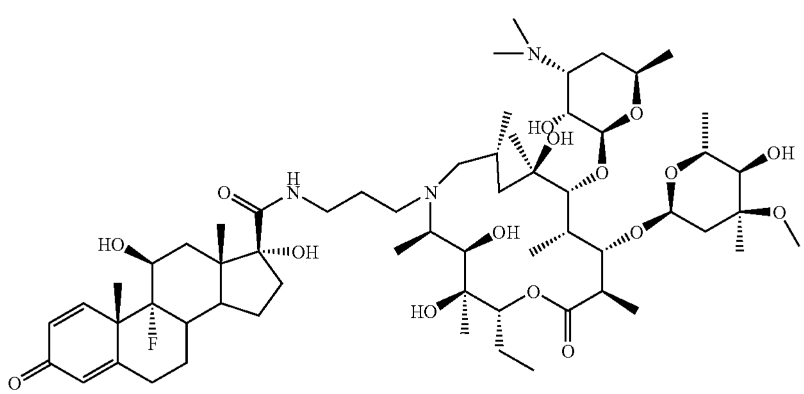 | $C_{60}H_{100}FN_3O_{16}$ | | 1139 |

TABLE 1-continued

| Comp. | Structure | Molecular formula | M.p. (° C.) | MH+ (ES+) |
|---|---|---|---|---|
| 7 | 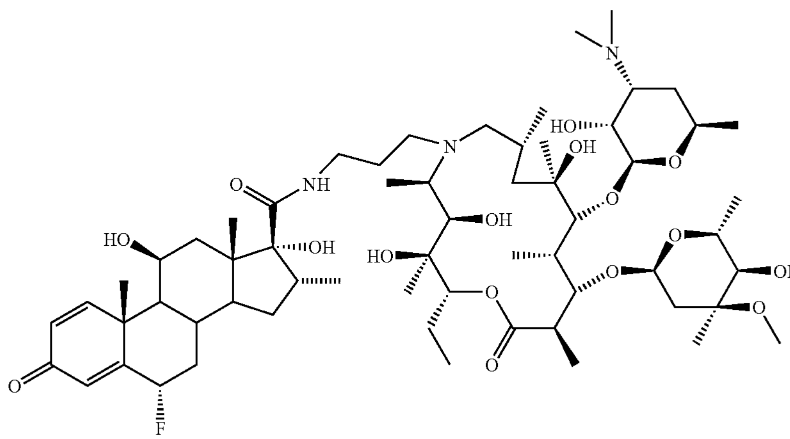 | $C_{61}H_{102}FN_3O_{16}$ | 175-178 | 1153 |
| 8 | 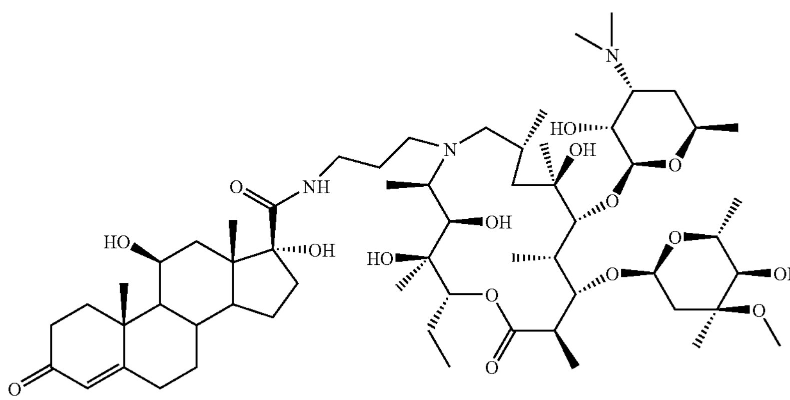 | $C_{60}H_{103}N_3O_{16}$ | 144 | 1123 |
| 9 | 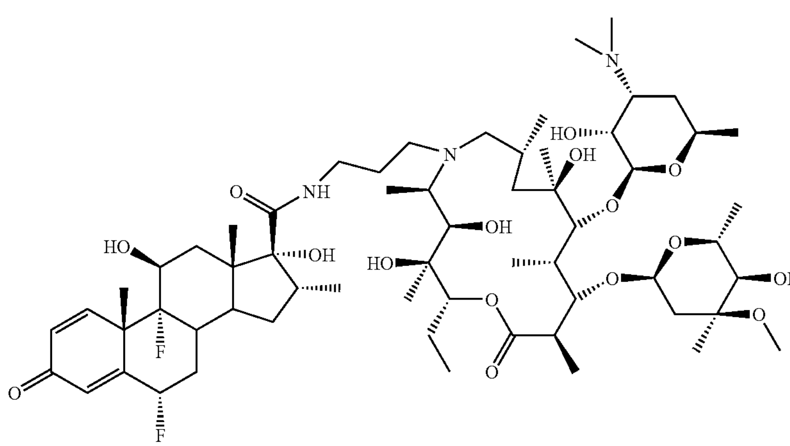 | $C_{61}H_{101}F_2N_3O_{16}$ | 169 | 1171 |

TABLE 1-continued
| Comp. | Structure | Molecular formula | M.p. (°C.) | MH+ (ES+) |
|---|---|---|---|---|
| 10 | 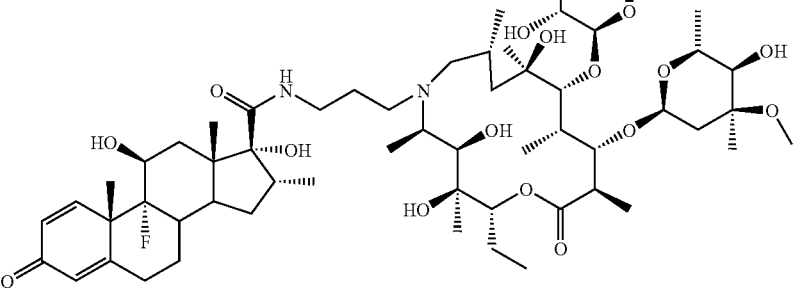 | $C_{61}H_{102}FN_3O_{16}$ | 170-175 | 1153 |
| 11 | 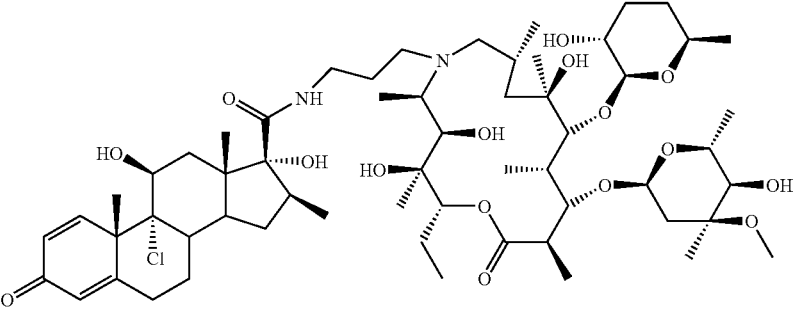 | $C_{61}H_{102}ClN_3O_{16}$ | — | 1169 |
| 12 | 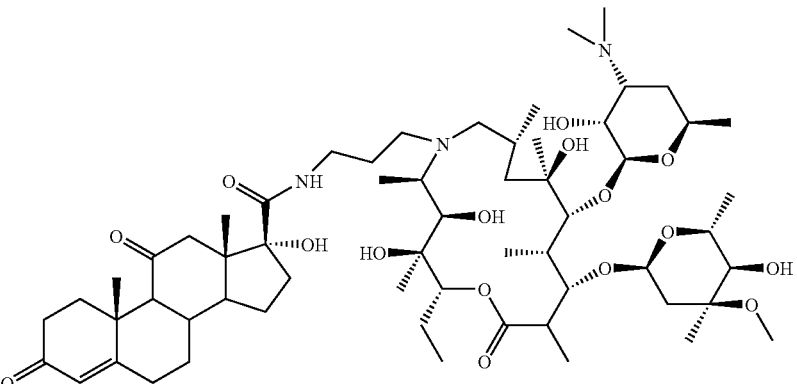 | $C_{60}H_{101}N_3O_{16}$ | — | 1121 |

TABLE 1-continued

| Comp. | Structure | Molecular formula | M.p. (° C.) | MH+ (ES+) |
|---|---|---|---|---|
| 13 | 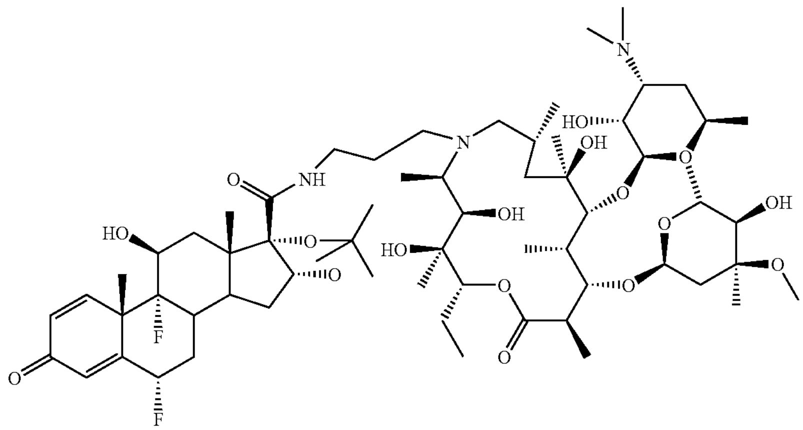 | $C_{63}H_{103}F_2N_3O_{17}$ | 178 | 1212 |
| 14 | 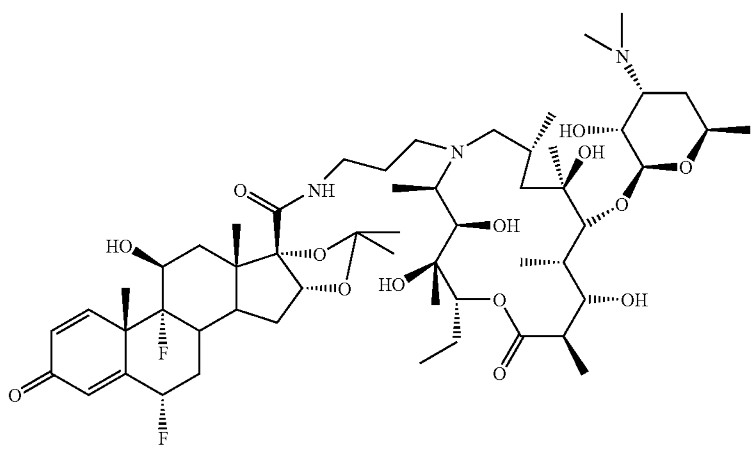 | $C_{55}H_{89}F2N_3O_{14}$ | — | 1055 |
| 15 | 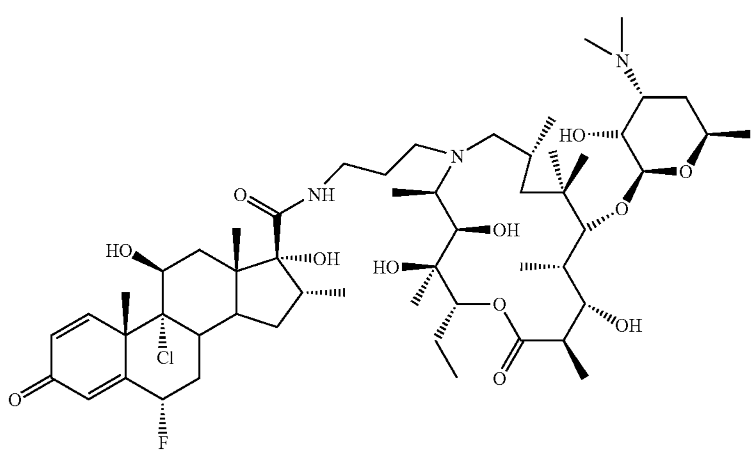 | $C_{53}H_{87}ClFN_3O_{13}$ | 130-132 | 1086 |

TABLE 1-continued

| Comp. | Structure | Molecular formula | M.p. (° C.) | MH+ (ES+) |
|---|---|---|---|---|
| 16 | 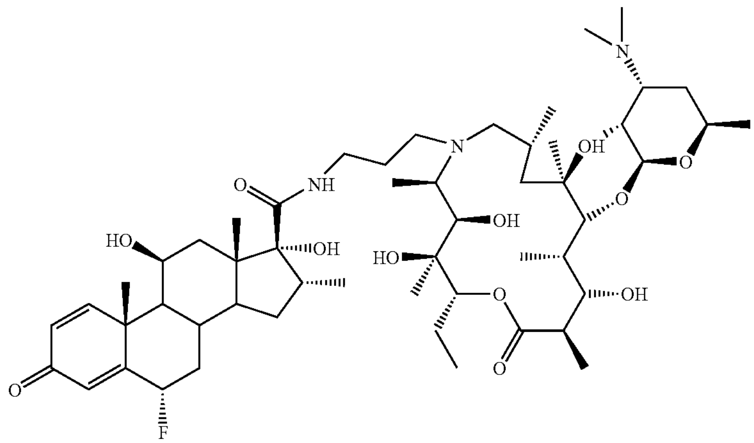 | $C_{53}H_{88}FN_3O_{13}$ | 202-204 | 995 |
| 17 | 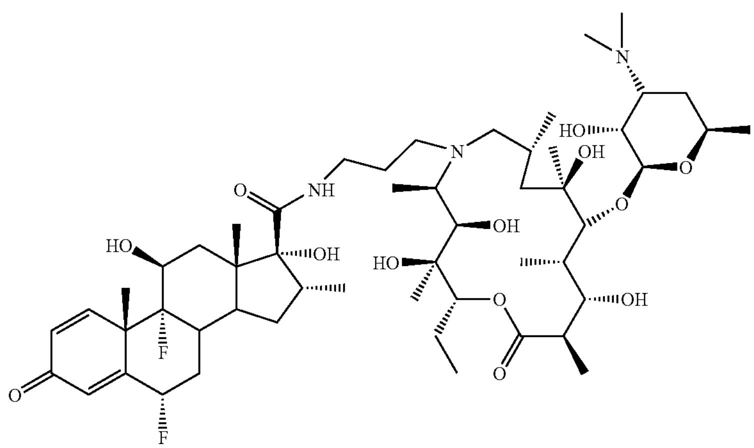 | $C_{53}H_{87}F_2N_3O_{13}$ | 182 | 1013 |
| 18 | 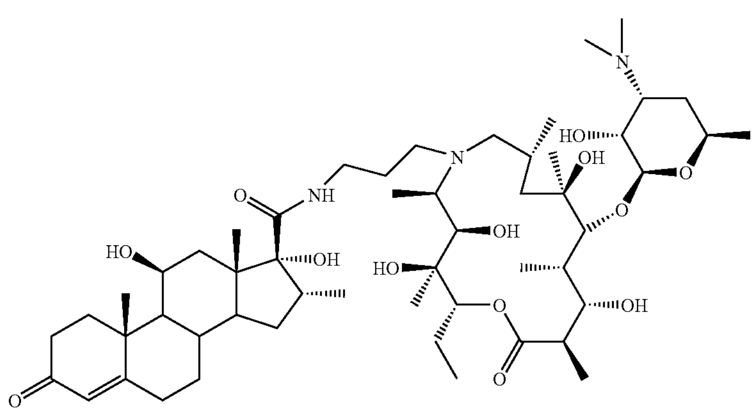 | $C_{52}H_{89}N_3O_{13}$ | 160-161 | 965 |

TABLE 1-continued

| Comp. | Structure | Molecular formula | M.p. (°C.) | MH+ (ES+) |
|---|---|---|---|---|
| 19 | 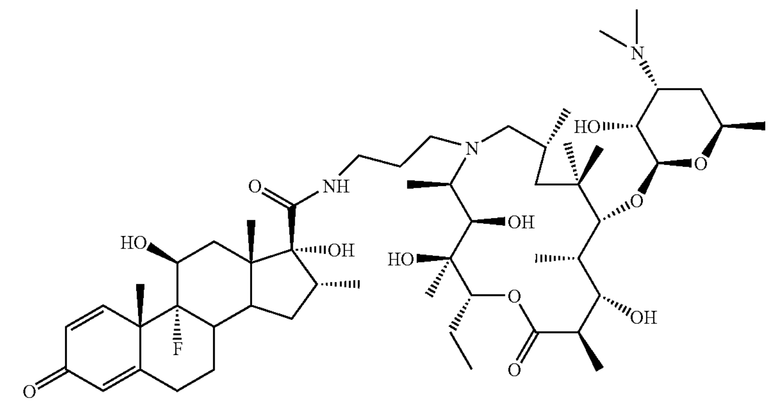 | $C_{53}H_{88}FN_3O_{13}$ | 260-265 | 995 |
| 20 | 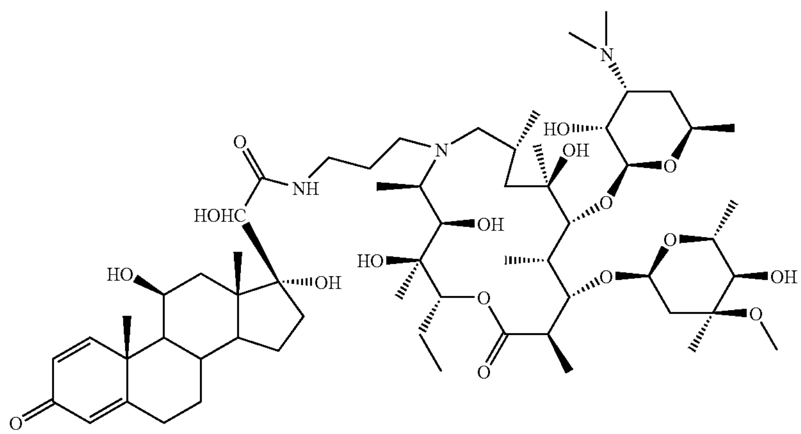 | $C_{61}H_{103}N_3O_{17}$ | | 1151 |
| 21 | 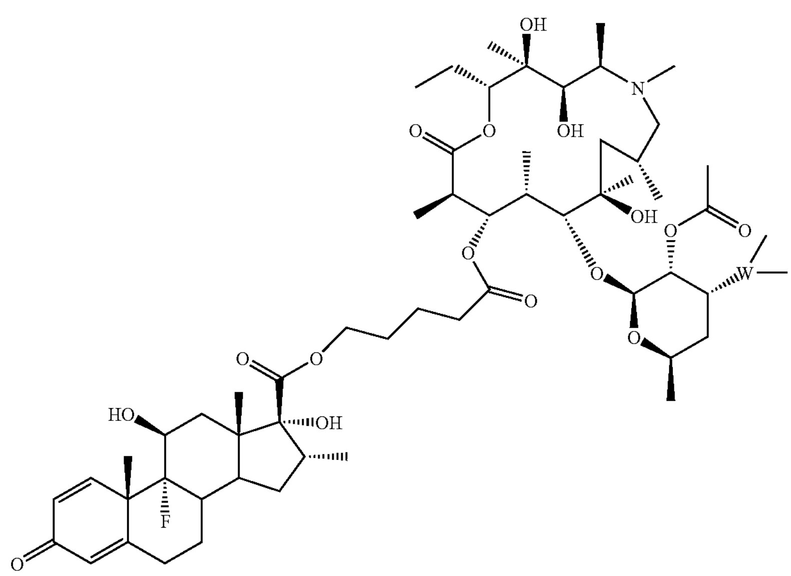 | $C_{58}H_{93}FN_2O_{16}$ | 174-175 | 1094 |

TABLE 1-continued
| Comp. | Structure | Molecular formula | M.p. (° C.) | MH+ (ES+) |
|---|---|---|---|---|
| 22 | 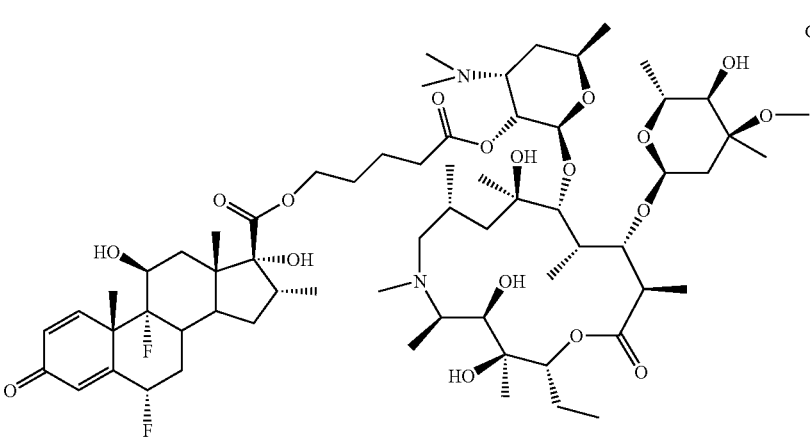 | $C_{64}H_{104}F_2N_2O_{18}$ | 159-160 | 1228 |
| 23 | 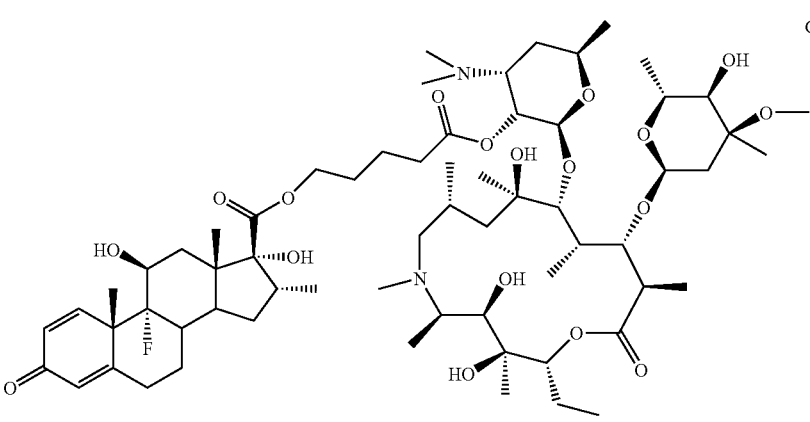 | $C_{64}H_{105}FN_2O_{18}$ | 161-168 | 1210 |
| 24 | 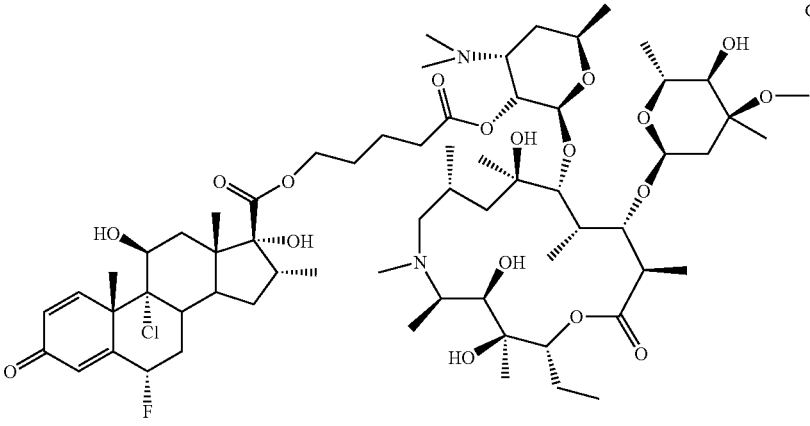 | $C_{64}H_{104}ClFN_2O_{18}$ | 91-99 | 1244 |

TABLE 1-continued

| Comp. | Structure | Molecular formula | M.p. (° C.) | MH+ (ES+) |
|---|---|---|---|---|
| 25 | 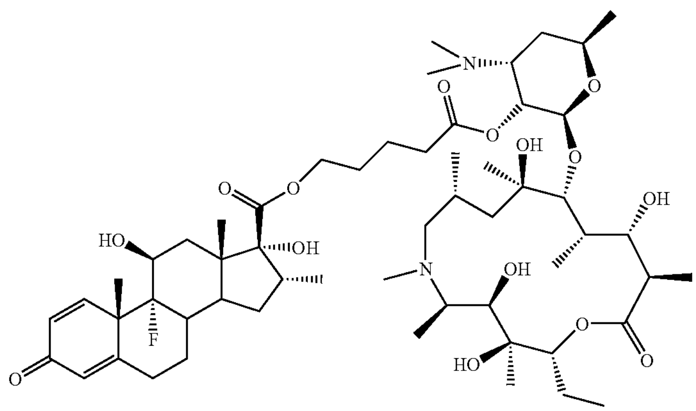 | $C_{56}H_{91}FN_2O_{15}$ | 170 | 1052 |
| 26 | 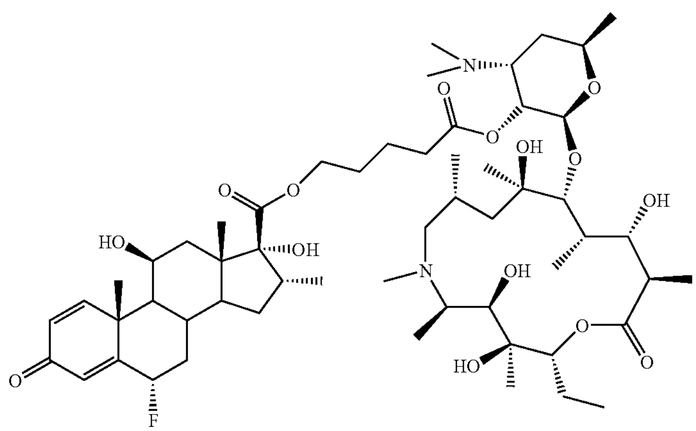 | $C_{56}H_{91}FN_2O_{15}$ | 145-151 | 1052 |
| 27 | 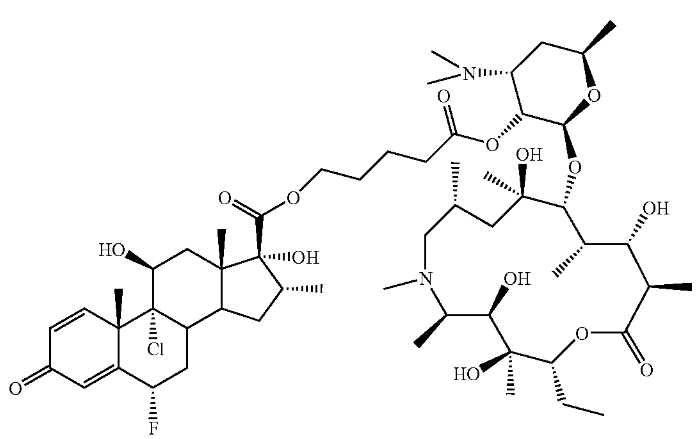 | $C_{56}H_{90}ClFN_2O_{15}$ | 130-132 | 1086 |

TABLE 1-continued

| Comp. | Structure | Molecular formula | M.p. (° C.) | MH+ (ES+) |
|---|---|---|---|---|
| 28 | 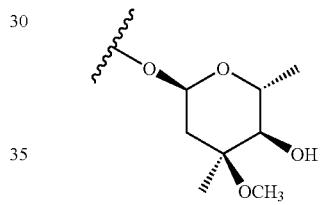 | $C_{53}H_{83}FN_2O_{15}$ | — | 1007 |

The invention claimed is:
1. A compound of the structure I

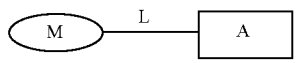

characterized in that M is a macrolide subunit selected from M1, M2, M3, M4, M5 and M6:

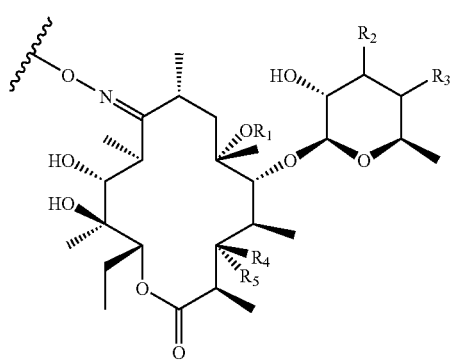

i)
wherein
$R_1$ is hydrogen or methyl group,
$R_2$ and $R_3$ are both hydrogen or together form a bond, or
   $R_2$ is an amino group represented by the substructure —NR'R"
     wherein R' and R" independently represent hydrogen, alkyl or cycloalkyl group having 1-6 carbon atoms, with the proviso that $R_3$ is then hydrogen, $R_4$ is a hydroxy or cladinosyl group represented by the structure

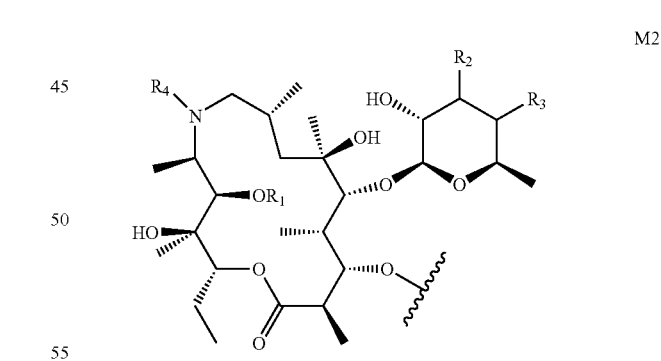

or $R_4$ and $R_5$ together form a carbonyl group, with the proviso that $R_1$ is then methyl group:

ii)
wherein
$R_1$ is hydrogen or methyl group,
$R_2$ and $R_3$ are both hydrogen or together form a bond, or
   $R_2$ is an amino group represented by the substructure —NR'R",
     wherein R' and R" independently represent hydrogen, alkyl or cycloalkyl group having 1-6 carbon atoms, with the proviso that $R_3$ is then hydrogen, R$_4$ represents alkyl group having 1-4 carbon atoms;

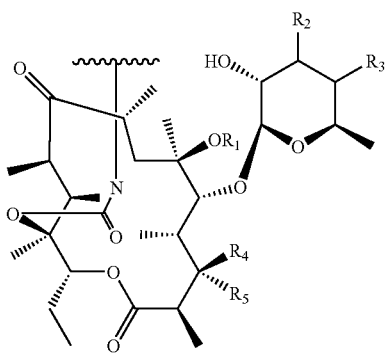

M3 iii)
wherein
R$_1$ is hydrogen or methyl group,
R$_2$ and R$_3$ are both hydrogen or together form a bond, or
R$_2$ is an amino group represented by the substructure
—NR'R",
wherein R'and R" independently represent hydrogen, alkyl or cycloalkyl group having 1-6 carbon atoms, with the proviso that R$_3$ is then hydrogen,
R$_4$ is a hydroxy or cladinosyl group represented by the structure

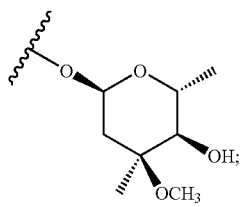

or R$_4$ and R$_5$ together form a carbonyl group, with the proviso that R$_1$ is then a methyl group;

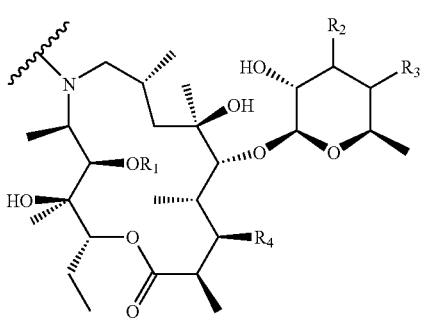

M4 iv)
wherein
R$_1$ is hydrogen or methyl group,
R$_2$ and R$_3$ are both hydrogen or together form a bond or
R$_2$ is an amino group represented by the substructure -NR'R";
wherein R' and R" independently represent hydrogen, alkyl or cycloalkyl group having 1-6 carbon atoms, with the proviso that R$_3$ is then hydrogen,
R$_4$ is a hydroxy or cladinosyl group represented by the structure

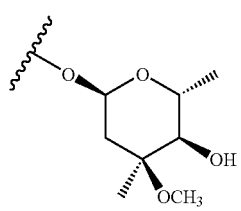

M5 v)
wherein
R$_1$ is hydrogen or a methyl group,
R$_2$ and R$_3$ are both hydrogen or together form a bond, or
R$_2$ is an amino group represented by the substructure -NR'R",
wherein R'and R"independently represent hydrogen, alkyl or cycloalkyl group having 1-6 carbon atoms, with the proviso that R$_3$ is then hydrogen.
R$_4$ is hydroxy or cladinosyl group represented by the structure:

$R_5$ represents alkyl group having 1-4 carbon atoms;

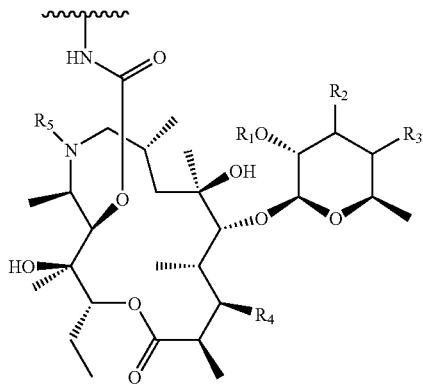

M6 vi) wherein
$R_1$ is hydrogen or an acetyl group,
$R_2$ and $R_3$ are both hydrogen or together form a bond, or
$R_2$ is an amino group represented by the substructure —NR'R",
wherein R' and R" independently represent hydrogen, alkyl or cycloalkyl group having 1-6 carbon atoms, with the proviso that $R_3$ is then hydrogen,
$R_4$ is hydroxy or cladinosyl group represented by the structure

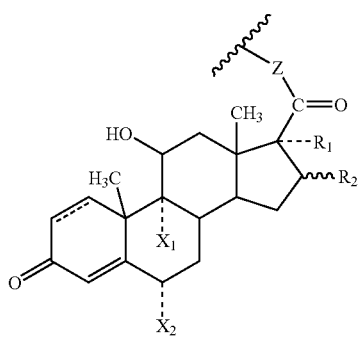

$R_5$ represents alkyl group having 1-4 carbon atoms;
A is an anti-inflammatory steroid subunit selected from the group consisting of A1, A2, A3, A4, A5 and A6 stereoisomeric forms thereof:

A1

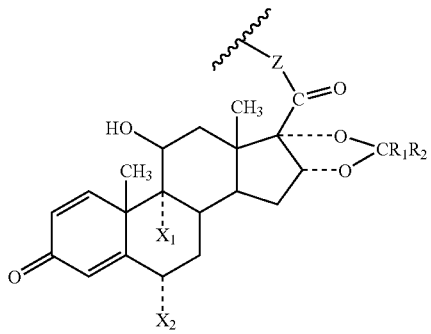

i) wherein
1,2-position represents a double or single carbon-carbon bond,
Z represents oxygen or NH group,
$R_1$ represents hydrogen, hydroxy, O-acyl or O-alkyl group,
$R_2$ represents hydrogen or methyl group oriented in α- or β-position,
$X_1$ represents hydrogen, fluorine, chlorine or bromine,
$X_2$ represents hydrogen, fluorine, chlorine or bromine;

A2

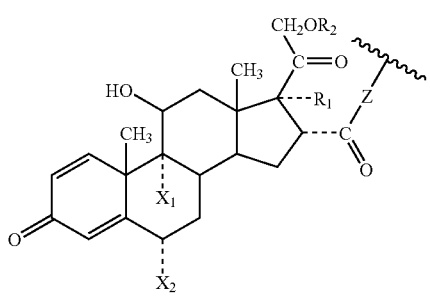

ii) wherein
Z represents oxygen or NH group,
$R_1$ represents hydrogen, hydroxy, O-acyl or O-alkyl group,
$R_2$ represents hydrogen or an acyl group,
$X_1$ represents hydrogen. fluorine, chlorine or bromine,
$X_2$ represents hydrogen, fluorine, chlorine or bromine;

A3 iii) wherein
the 1,2-position represents a double or single carbon-carbon bond,
Z represents oxygen or NH group,
$R_1$ represents hydrogen, a straight or branched hydrocarbon chain having 1-4 carbon atoms,
$R_2$ represents hydrogen, a straight or branched hydrocarbon chain having 1-10 carbon atoms, with the proviso that R, and $R_2$ are not simultaneously hydrogen,
$X_1$ represents hydrogen, fluorine, chlorine or bromine, $X_2$ represents hydrogen, fluorine, chlorine or bromine;

A4 iv) wherein
the 1,2-position represents a double or single carbon-carbon bond,
Z represents oxygen or NH group,
$R_1$ represents hydrogen, a straight or branched hydrocarbon chain having 1-4 carbon atoms,
$R_2$ represents hydrogen, a straight or branched hydrocarbon chain having 1-10 carbon atoms, with the proviso that $R_1$ and $R_2$ are not simultaneously hydrogen,
$X_1$ represents hydrogen, fluorine, chlorine or bromine,
$X_2$ represents hydrogen, fluorine, chlorine or bromine;

A5 v) wherein
the 1,2-position represents a double or single carbon-carbon bond,
$R_1$ represents hydrogen, a straight or branched hydrocarbon chain having 1-4 carbon atoms,
$R_2$ represents hydrogen, a straight or branched hydrocarbon chain having 1-10 carbon atoms, with the proviso that $R_1$ and $R_2$ are not simultaneously hydrogen,
$X_1$ represents hydrogen, fluorine, chlorine or bromine,
$X_2$ represents hydrogen, fluorine, chlorine or bromine;

A6 vi) wherein
1,2-position represents a double or single carbon-carbon bond,
Z represents oxygen or NH group,
$R_1$ represents hydrogen or hydroxy group, O-acyl or O-alkyl group,
$R_2$ represents hydrogen or a methyl group oriented in α- or β-position,
$R_3$ represents hydrogen or a radical of an acid having 1-4 carbon atoms,
$X_1$ is hydrogen, fluorine, chlorine or bromine,
$X_2$ is hydrogen, fluorine, chlorine or bromine;
L is a chain linking subunit M with A of the formula:
—$CR_1R_2(CR_3R_4)_nCR_5R_6$—,
wherein
n is 1-10,
$R_1$, $R_2$, $R_3$, $R_4$, $R_5$, $R_6$ represent hydrogen, $C_1$-$C_4$alkyl, aryl, metoxy, halogen,
hydroxy or mercapto group, and one or more —$CR_3R_4$- groups is optionally substituted with oxygen, sulphur, an aromatic nucleus or an amino group additionally bearing hydrogen or a $C_1$-$C_4$ alkyl or aryl group with the proviso that at least one methylene group is situated at the end of the linking L group, or
$R_1$, $R_2$, $R_3$, $R_4$, $R_5$, $R_6$ together form one or more double or triple bonds in a chain, thus forming alkenyl or alkinyl, with the proviso that at least one methylene group is situated at the end of linking L group;
or a salt or solvate thereof.

2. The compound according to claim 1, characterized in that:
M is M1, wherein $R_1$ is a methyl group. $R_2$ is a dimethylamino group, $R_3$ is hydrogen, $R_4$ is cladinose, or $R_4$ and $R_5$ together form a carbonyl group;
A is selected from:
i) A1, wherein Z represents oxygen or NH group, $R_1$, is hydroxy group, or O-alkyl group having 1-4 carbon atoms, $R_2$ is hydrogen or methyl group, $X_1$ is hydrogen or fluorine and $X_2$ is hydrogen;
ii) A2, wherein Z represents oxygen or NH group, $R_1$ is hydrogen, $R_2$ is hydrogen, $X_1$ is fluorine and $X_2$ is hydrogen;
iii) A3, wherein Z represents oxygen or NH group, 1,2-position is a double carbon-carbon bond, $R_1$ and $R_2$ are methyl groups, $X_1$ is fluorine and $X_2$ is fluorine;
iv) A4, wherein Z represents oxygen or NH group, 1,2-position is a double carbon-carbon bond, $R_1$ and $R_2$ are methyl groups, $X_1$ is fluorine and $X_2$ is fluorine; and
v) A6, wherein Z represents oxygen or NH group, 1,2-position is a double carbon-carbon bond, $R_1$ is hydroxy group, $R_2$ is hydrogen or a methyl group in α- or β-position, $R_3$ is hydrogen, $X_1$ is hydrogen, fluorine or chlorine and $X_2$ is hydrogen or fluorine; and
L is —$CR_1R_2(CR_3R_4)_nCR_5R_6$—, wherein n is 1-10 and $R_1$, $R_2$, $R_3$ and $R_4$ are each hydrogen.

3. The compound according to claim 1, characterized in that: M is M2, wherein $R_1$ is hydrogen, $R_2$ is a dimethylamino group, $R_3$ is hydrogen, $R_4$ is methyl;
A is selected from:
i) A1, wherein Z represents oxygen or NH group, $R_1$ is hydroxy group, or O-alkyl group having 1-4 carbon atoms, $R_2$ is hydrogen or methyl group, $X_1$ is hydrogen or fluorine and $X_2$ is hydrogen;
ii) A2, wherein Z represents oxygen or NH group, $R_1$ is hydrogen, $R_2$ is hydrogen, $X_1$ is fluorine and $X_2$ is hydrogen;

iii) A3, wherein Z represents oxygen or NH group, 1,2-position is a double carbon-carbon bond, $R_1$ and R2 are methyl groups, $X_1$ is fluorine and $X_2$ is fluorine;

iv) A4, wherein Z represents oxygen or NH group, 1,2-position is a double carbon-carbon bond, $R_1$ and $R_2$ are methyl groups, $X_1$ is fluorine and $X_2$ is fluorine; and v) A6, wherein Z represents oxygen or NH group, 1,2-position is a double carbon-carbon bond, $R_1$ is hydroxy group, $R_2$ is hydrogen or a methyl group in α- or β-position, $R_3$ is hydrogen, $X_1$ is hydrogen, fluorine or chlorine and $X_2$ is hydrogen or fluorine; and L is —$CR_1R_2(CR_3R_4CR_5R_6$—, wherein n is 1-10 and $R_1$, $R_2$, $R_3$ and $R_4$ are each hydrogen.

4. The compound according to claim 1, characterized in that:

M is M3, wherein $R_1$ is hydrogen, $R_2$ is a dimethylamino group, $R_3$ is hydrogen, $R_4$ and $R_5$ together form a carbonyl group;

A is selected from:

i) A1, wherein Z represents oxygen or NH group, $R_1$ is hydroxy group, or O-alkyl group having 1-4 carbon atoms, $R_2$ is hydrogen or methyl group, $X_1$ is hydrogen or fluorine and $X_2$ is hydrogen;

ii) A2, wherein Z represents oxygen or NH group, $R_1$ is hydrogen, $R_2$ is hydrogen, $X_1$ is fluorine and $X_2$ is hydrogen;

iii) A3, wherein Z represents oxygen or NH group, 1,2-position is a double carbon-carbon bond, $R_1$ and $R_2$ are methyl groups, $X_1$ is fluorine and $X_2$ is fluorine;

iv) A4, wherein Z represents oxygen or NH group, 1,2-position is a double carbon-carbon bond, $R_1$ and K are methyl groups, $X_1$ is fluorine and $X_2$ is fluorine; and v) A6, wherein Z represents oxygen or NH group, 1,2-position is a double carbon-carbon bond, $R_1$ is hydroxy group, $R_2$ is hydrogen or a methyl group in α- or β-position, $R_3$ is hydrogen, $X_1$ is hydrogen, fluorine or chlorine and $X_2$ is hydrogen or fluorine; and L is —$CR_1R_2(CR_3R_4)_nCR_5R_6$—, wherein n is 1-10 and $R_1$, $R_2$, $R_3$ and $R_4$ are each hydrogen.

5. The compound according to claim 1, characterized in that:

M is M4, wherein $R_1$ is hydrogen, $R_2$ is a dimethylamino group, $R_3$ is hydrogen, $R_4$ is cladinose or hydroxy group;

A is selected from:

i) A1, wherein Z represents oxygen or NH group, $R_1$ is hydroxy group, or O-alkyl group having 1-4 carbon atoms, $R_2$ is hydrogen or methyl group, $X_1$ is hydrogen or fluorine and $X_2$ is hydrogen;

ii) A2, wherein Z represents oxygen or NH group, $R_1$ is hydrogen, $R_2$ is hydrogen, $X_1$ is fluorine and $X_2$ is hydrogen;

iii) A3, wherein Z represents oxygen or NH group, 1,2-position is a double carbon-carbon bond, $R_1$ and $R_2$ are methyl groups, $X_1$ is fluorine and $X_2$ is fluorine;

iv) A4, wherein Z represents oxygen or NH group, 1,2-position is a double carbon-carbon bond, $R_1$ and $R_2$ are methyl groups, $X_1$ is fluorine and $X_2$ is fluorine; and v) A6, wherein Z represents oxygen or NH group, 1,2-position is a double carbon-carbon bond, $R_1$ is hydroxy group, $R_2$ is hydrogen or a methyl group in α- or β-position, $R_3$ is hydrogen, $X_1$ is hydrogen, fluorine or chlorine and $X_2$ is hydrogen or fluorine; and L is —$CR_1R_2(CR_3R_4)_nCR_5R_6$—, wherein n is 2-10 and $R_1$, $R_2$, $R_3$ and $R_4$ are each hydrogen.

6. The compound according to claim 1, characterized in that:

M is M5, wherein $R_1$ is hydrogen, $R_2$ is a dimethylamino group, $R_3$ is hydrogen, $R_4$ is a cladinose or hydroxy group and $R_5$ is a methyl group;

A is selected from:

i) A1, wherein Z represents oxygen or NH group, $R_1$ is hydroxy group, or O-alkyl group having 1-4 carbon atoms, $R_2$ is hydrogen or methyl group, $X_1$ is hydrogen or fluorine and $X_2$ is hydrogen;

ii) A2, wherein Z represents oxygen or NH group, $R_1$ is hydrogen, $R_2$ is hydrogen, $X_1$ is fluorine and $X_2$ is hydrogen;

iii) A3, wherein Z represents oxygen or NH group, 1,2-position is a double carbon-carbon bond, $R_1$ and $R_2$ are methyl groups, $X_1$ is fluorine and $X_2$ is fluorine;

iv) A4, wherein Z represents oxygen or NH group, 1,2-position is a double carbon-carbon bond, $R_1$ and $R_2$ are methyl groups, $X_1$ is fluorine and $X_2$ is fluorine; and v) A6, wherein Z represents oxygen or NH group, 1,2-position is a double carbon-carbon bond, $R_1$ is hydroxy group, $R_2$ is hydrogen or a methyl group in α- or β-position, $R_3$ is hydrogen, $X_1$ is hydrogen, fluorine or chlorine and $X_2$ is hydrogen or fluorine; and L is —$CR_1R_2(CR_3R_4)_nCR_5R_6$—, wherein n is 2-10 and $R_1$, $R_2$, $R_3$ and $R_4$ are each hydrogen.

7. The compound according to claim 1, characterized in that:

M is M6, wherein $R_1$ is hydrogen, $R_2$ is a dimethylamino group, $R_3$ is hydrogen, $R_4$ is cladinose or hydroxy group and $R_5$ is a methyl group;

A is selected from:

i) A1, wherein Z represents oxygen or NH group, $R_1$ is hydroxy group, or O-alkyl group having 1-4 carbon atoms, $R_2$ is hydrogen or methyl group, $X_1$ is hydrogen or fluorine and $X_2$ is hydrogen;

ii) A2, wherein Z represents oxygen or NH group, $R_1$ is hydrogen, $R_2$ is hydrogen, $X_1$ is fluorine and $X_2$ is hydrogen;

iii) A3, wherein Z represents oxygen or NH group, 1,2-position is a double carbon-carbon bond, $R_1$ and $R_2$ are methyl groups, $X_1$ is fluorine and $X_2$ is fluorine;

iv) A4, wherein Z represents oxygen or NH group, 1,2-position is a double carbon-carbon bond, $R_1$ and $R_2$ are methyl groups, $X_1$ is fluorine and $X_2$ is fluorine; and v) A6, wherein Z represents oxygen or NH group, 1,2-position is a double carbon-carbon bond, $R_1$ is hydroxy group, $R_2$ is hydrogen or a methyl group in α- or β-position, $R_3$ is hydrogen, $X_1$ is hydrogen, fluorine or chlorine and $X_2$ is hydrogen or fluorine; and L is —$CR_1R_2(CR_3R_4)_nCR_5R_6$—, wherein n is 2-10 and $R_1$, $R_2$, $R_3$ and $R_4$ are each hydrogen.

8. The compound according to claim 1 having the formula (1):
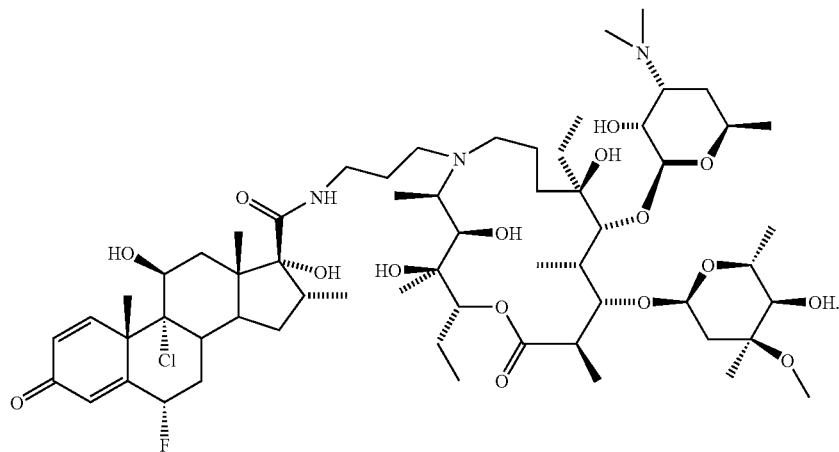
9. The compound according to claim 1 having the formula (2):
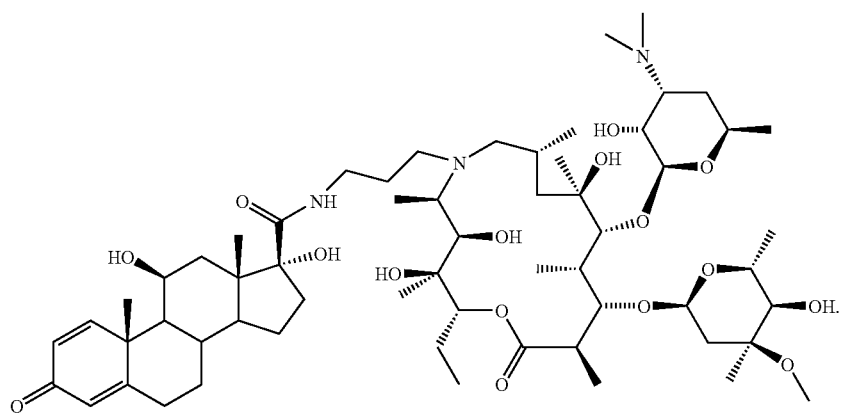
10. The compound according to claim 1 having the formula (3):
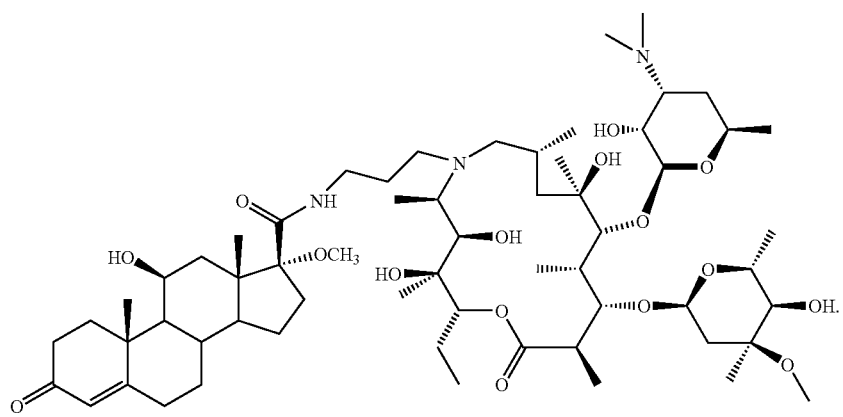

11. The compound according to claim 1 having the formula (4):
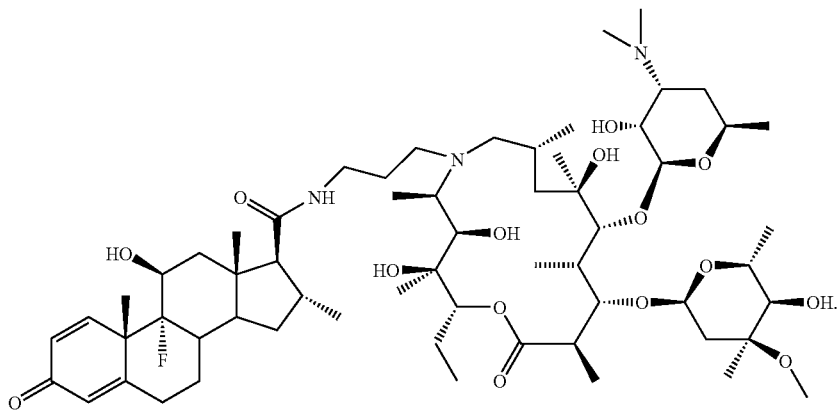
12. The compound according to claim 1 having the formula (5):
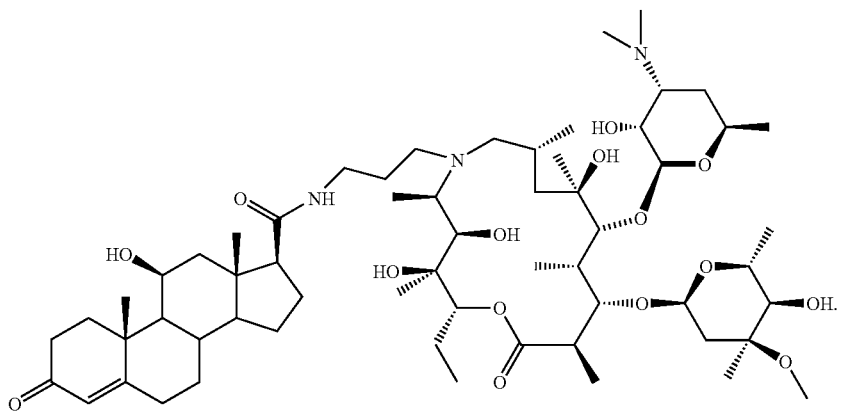
13. The oompound according to claim 1 having the formula (6):
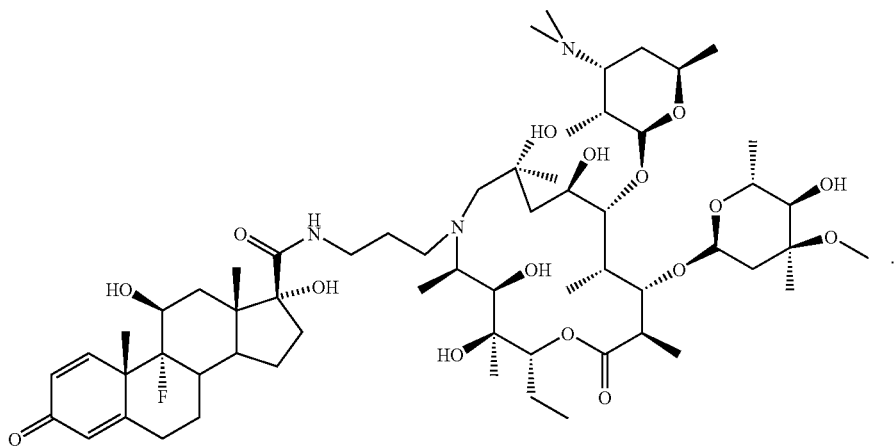

14. The compound according to claim 1 having the formula (7):
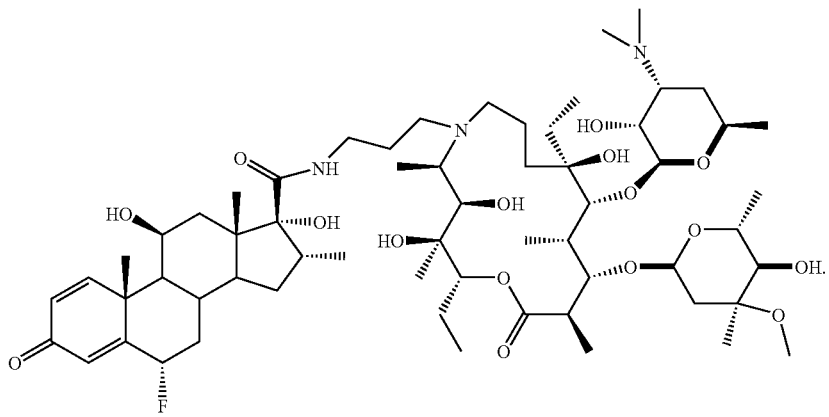
15. The compound according to claim 1 having the formula (8):
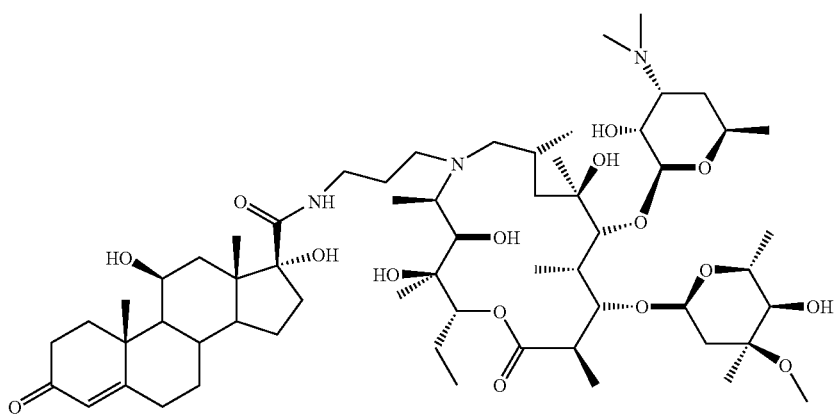
16. The compound according to claim 1 having the formula (9):
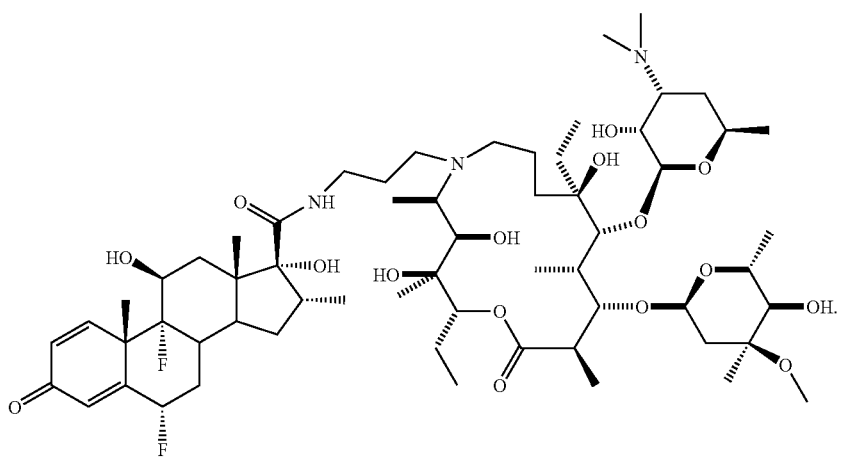

17. The compound according to claim 1 having the formula (10):
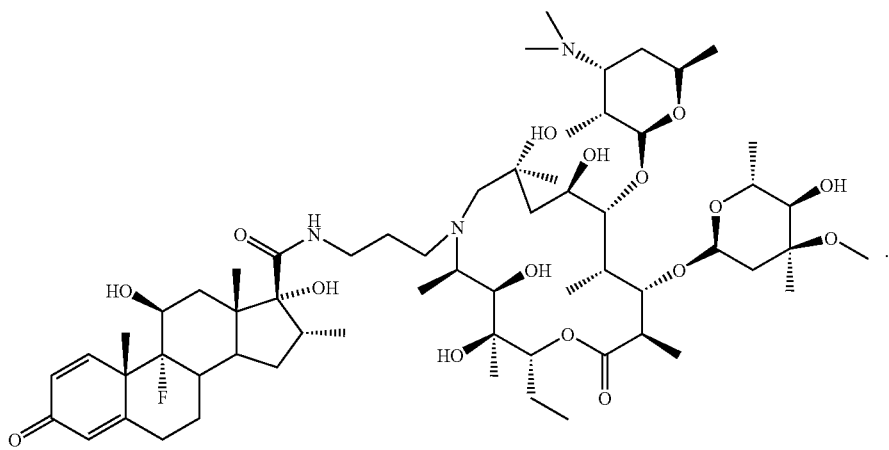
18. The compound according to claim 1 having the formula (11):
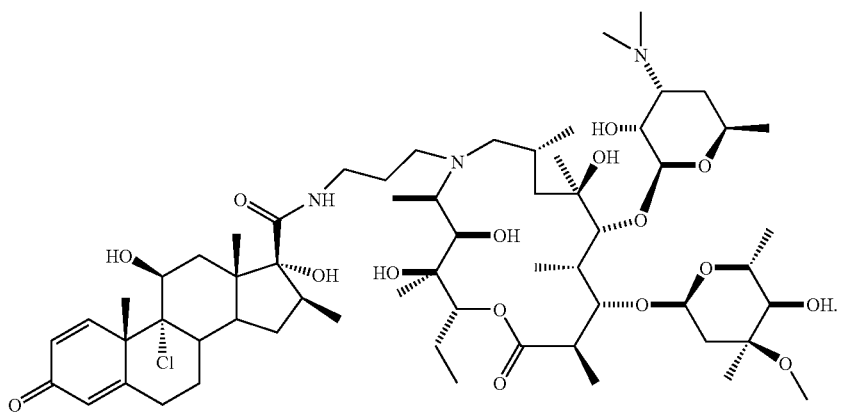
19. The compound according to claim 1 having the formula (12):
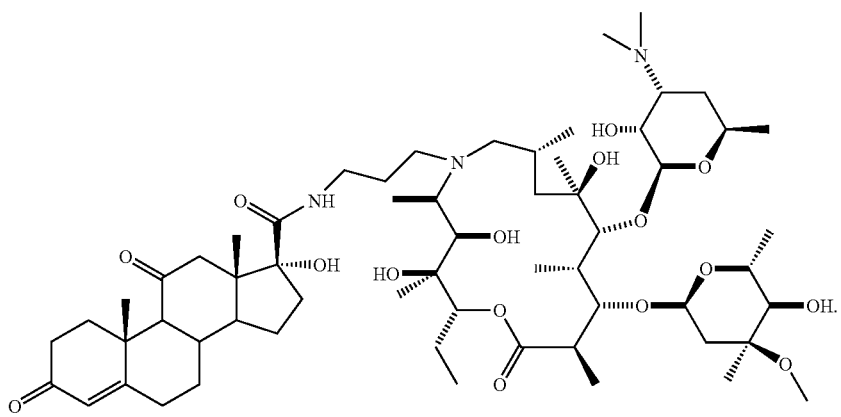

20. The compound according to claim 1 having the formula (13):
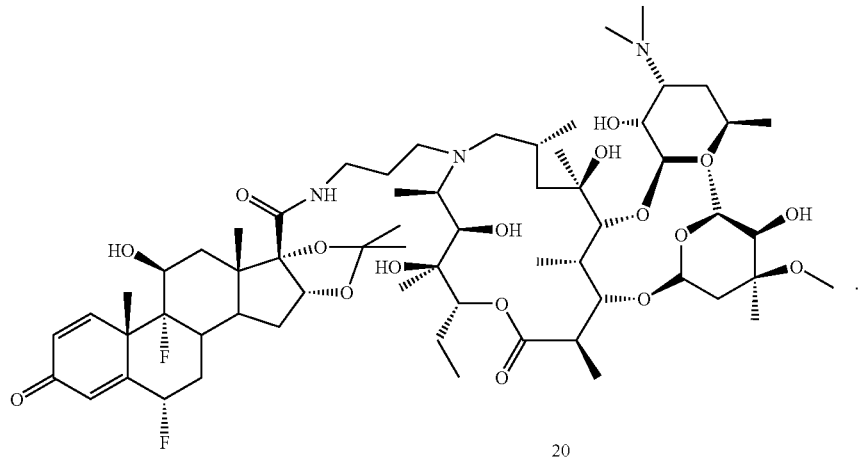
21. The compound according to claim 1 having the formula (14):
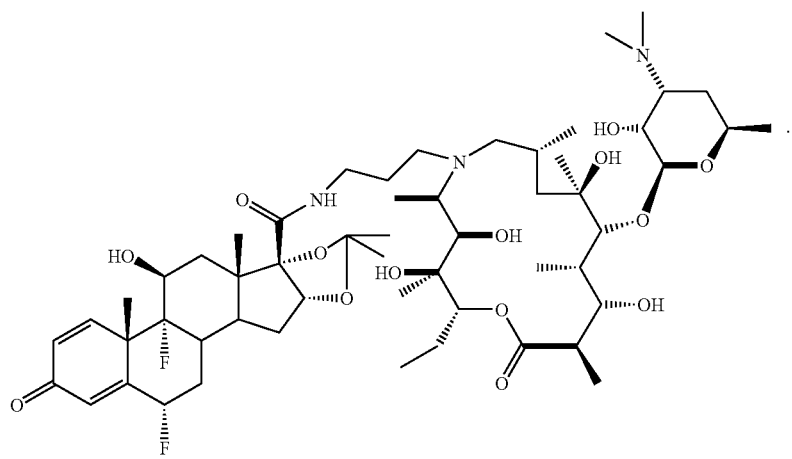
22. The compound according to claim 1 having the formula (15):
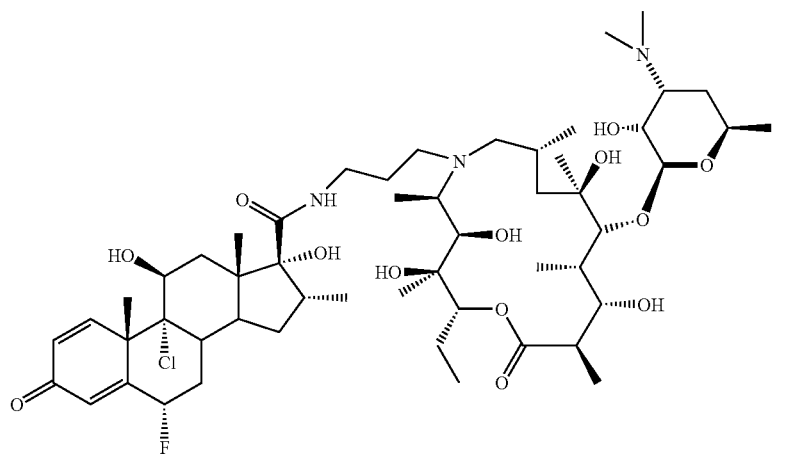

23. The compound according to claim 1 having the formula (16):
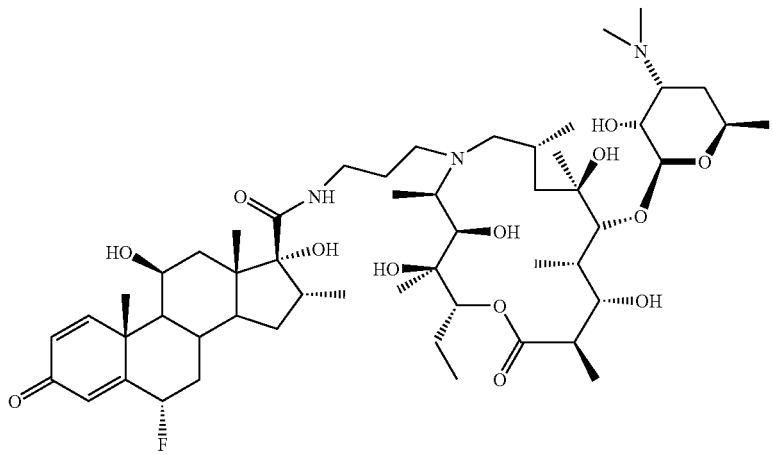
24. The compound according to claim 1 having the formula (17):
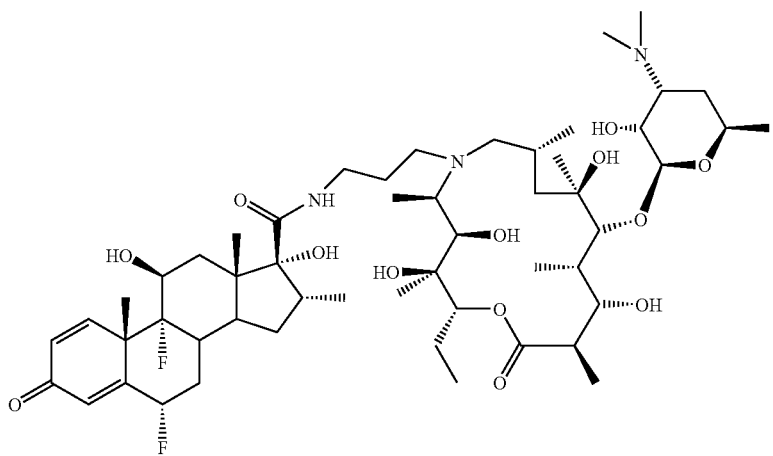
25. The compound according to claim 1 having the formula (18):
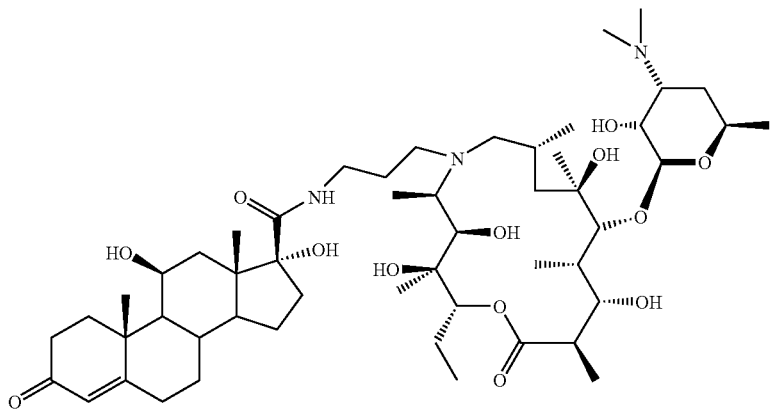

26. The compound according to claim 1 having the formula (19):
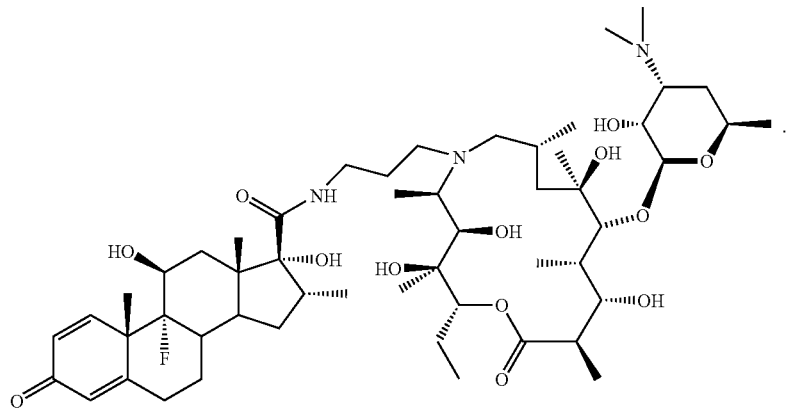
27. The compound according to claim 1 having the formula (20):
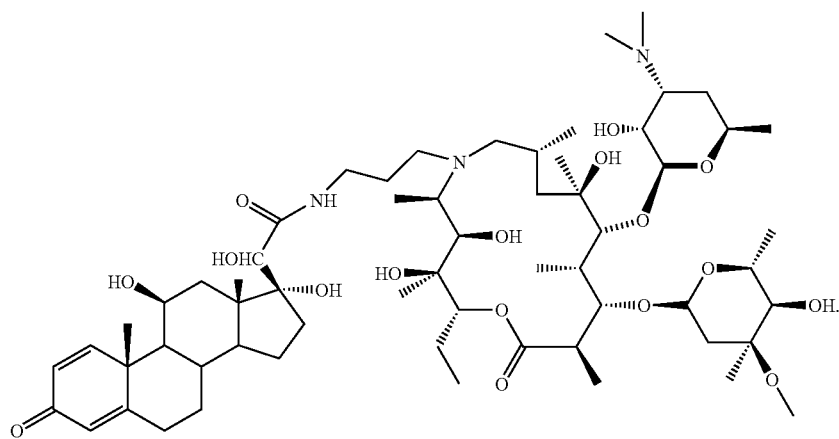

28. The compound according to claim 1 having the formula (21):
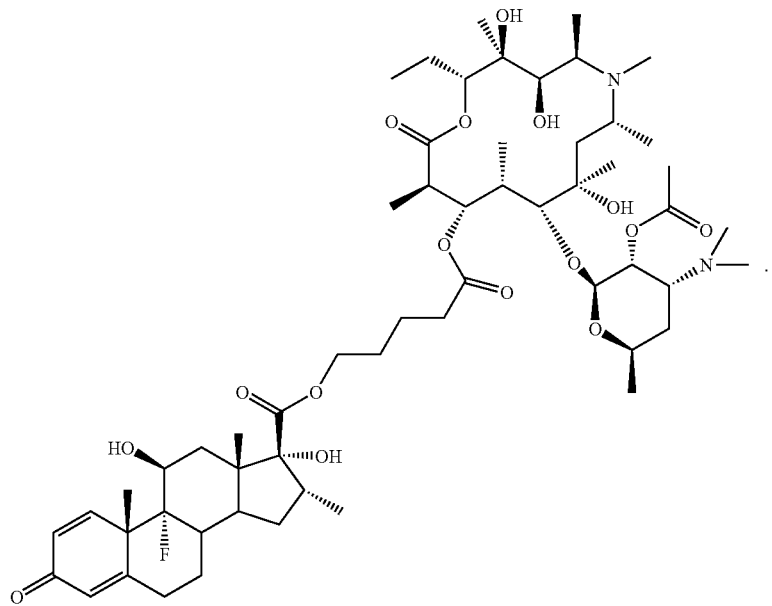
29. The compound according to claim 1 having the formula (22):
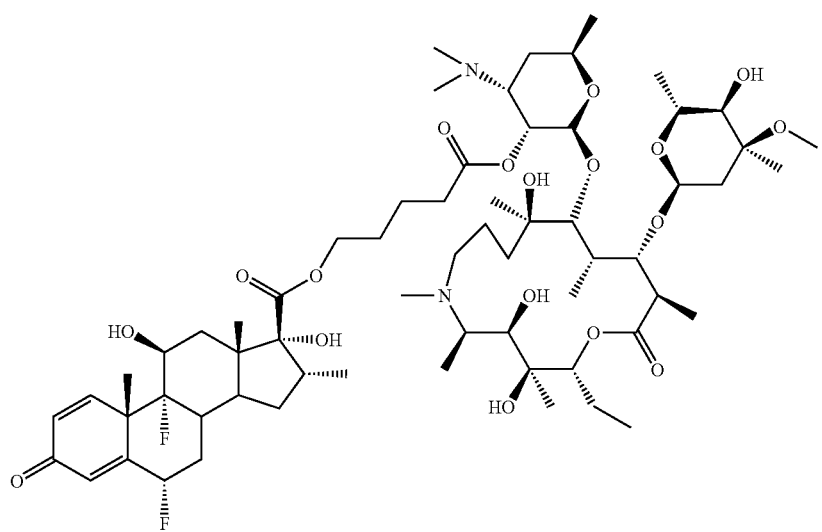

30. The compound according to claim 1 having the formula (23):
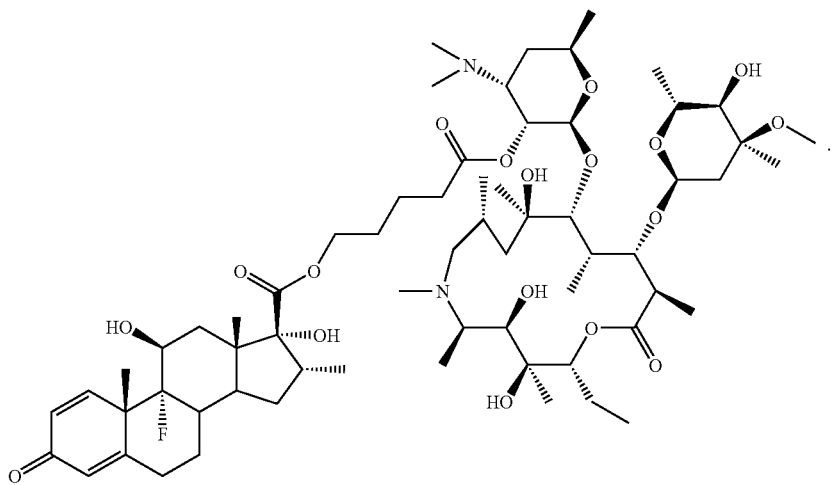
31. The compound according to claim 1 having the formula (24):
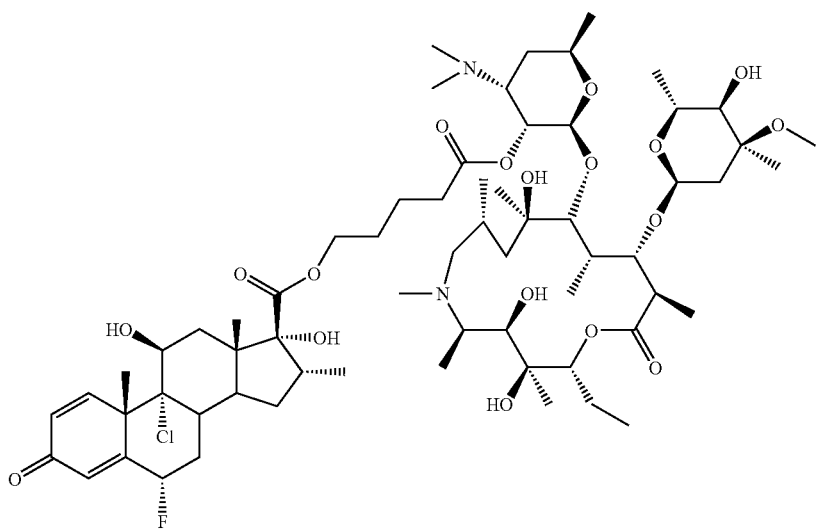

32. The compound according to claim 1 having the formula (25):
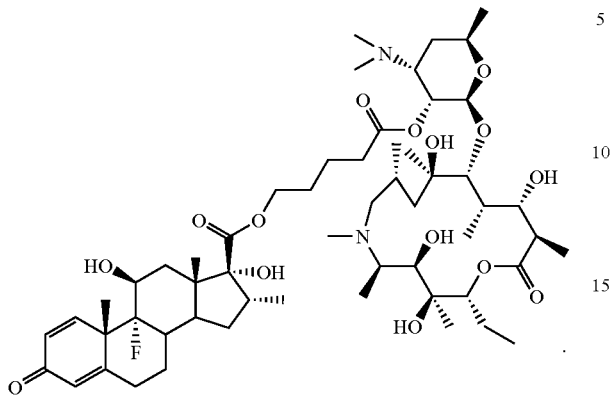
33. The compound according to claim 1 having the formula (26):
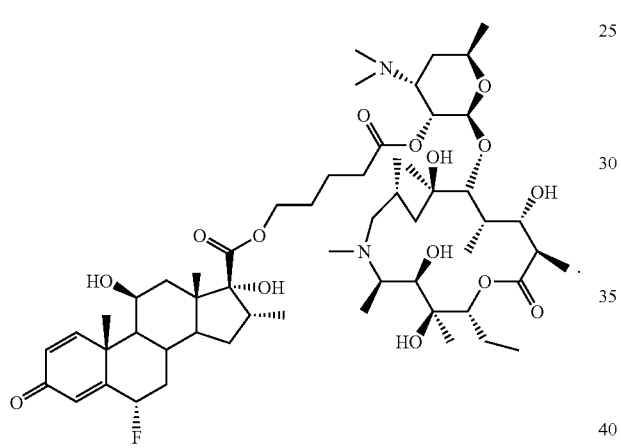
34. The compound according to claim 1 having the formula (27):
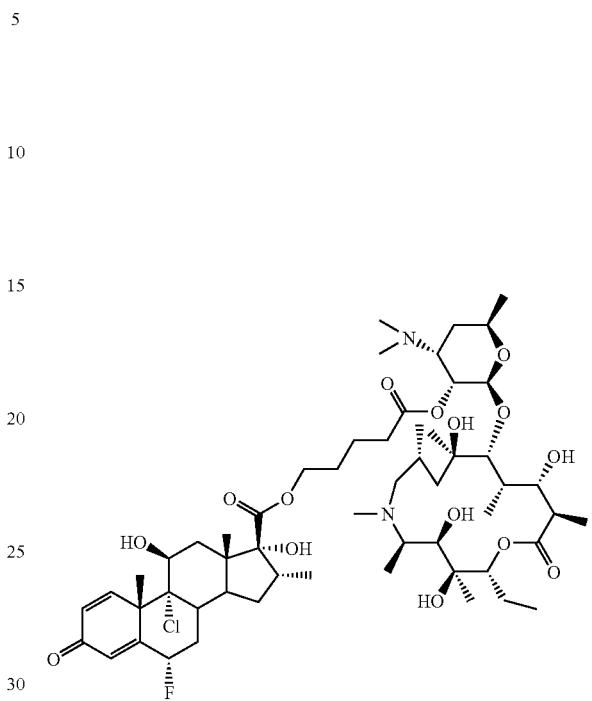
35. The compound according to claim 1 having the formula (28):
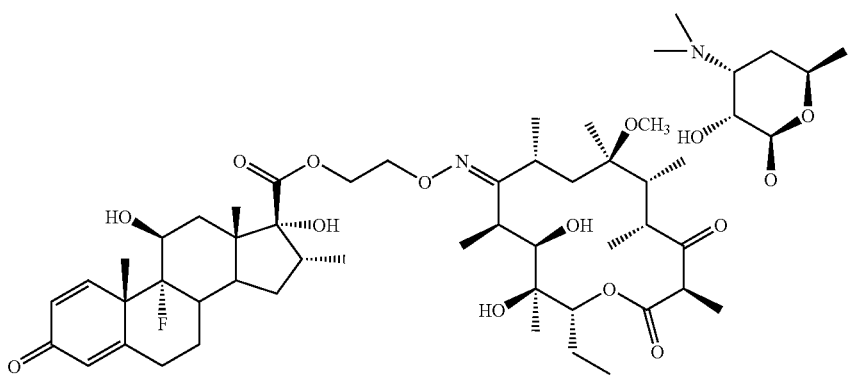

36. A method for the treatment of an inflammatory condition or disease induced by excessive nonregulated production of cytokines and inflammation mediators comprising administration to a human or animal body in need of such treatment an effective amount of a compound according to claim 1.

37. The method according to claim 36 wherein said inflammatory condition or disease is selected from asthma, chronic obstructive pulmonary disease, allergic rhinitis, nasal polyps, Crohn's disease, colitis, ulcerative colitis, eczema, psoriasis, allergic dermatitis, neurodermatitis, pruritis, conjunctivitis and rheumatoid arthritis.

38. The compound according to claim 1, characterized in that: M is M1.

39. The compound according to claim 1, characterized in that: M is M2.

40. The compound according to claim 1, characterized in that: M is M3.

41. The compound according to claim 1, characterized in that: M is M4.

42. The compound according to claim 1, characterized in that: M is M5.

43. The compound according to claim 1, characterized in that: M is M6.

* * * * *

UNITED STATES PATENT AND TRADEMARK OFFICE
CERTIFICATE OF CORRECTION

PATENT NO. : 7,446,097 B2  Page 1 of 1
APPLICATION NO. : 10/250934
DATED : November 4, 2008
INVENTOR(S) : Mercep et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 742 days Delete the phrase "by 742 days" and insert -- by 647 days --

Signed and Sealed this

Thirteenth Day of October, 2009

David J. Kappos
*Director of the United States Patent and Trademark Office*